US012758192B2

(12) United States Patent
Kubota et al.

(10) Patent No.: US 12,758,192 B2
(45) Date of Patent: Oct. 13, 2026

(54) ULTRASOUND DIAGNOSTIC SYSTEM AND IMAGE PROCESSING APPARATUS

(71) Applicant: FUJIFILM Corporation, Tokyo (JP)

(72) Inventors: Hidenao Kubota, Tokyo (JP); Katsunori Asafusa, Tokyo (JP); Hirohiko Narita, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/825,811

(22) Filed: Sep. 5, 2024

(65) Prior Publication Data

US 2025/0090141 A1 Mar. 20, 2025

(30) Foreign Application Priority Data

Sep. 14, 2023 (JP) ................................ 2023-149571

(51) Int. Cl.
*A61B 8/00* (2006.01)

(52) U.S. Cl.
CPC ............ *A61B 8/5207* (2013.01); *A61B 8/463* (2013.01); *A61B 8/464* (2013.01); *A61B 8/466* (2013.01); *A61B 8/467* (2013.01); *A61B 8/565* (2013.01)

(58) Field of Classification Search
None
See application file for complete search history.

(56) References Cited

U.S. PATENT DOCUMENTS

2014/0058266 A1* 2/2014 Call .................... G01S 15/8915 600/443
2017/0219704 A1* 8/2017 Call ........................ G01S 15/89
2020/0022678 A1* 1/2020 McLaughlin ............ A61B 8/54

FOREIGN PATENT DOCUMENTS

JP 2009-112357 A 5/2009
JP 2024029688 A * 3/2024

* cited by examiner

*Primary Examiner* — Michael J Carey
*Assistant Examiner* — Marjan Saboktakin

(57) ABSTRACT

An ultrasound image different from an ultrasound image displayed on an ultrasound diagnostic apparatus can be provided to a person in a remote location as close to real time as possible. An ultrasound diagnostic apparatus acquires Raw data by transmitting and receiving ultrasonic waves, and generates a first ultrasound image by applying first image processing to the Raw data. The Raw data is transmitted from the ultrasound diagnostic apparatus to an image processing apparatus via a communication path including a high-speed communication path. The image processing apparatus generates a second ultrasound image by applying second image processing different from the first image processing to the Raw data. The second ultrasound image is displayed on a display of the image processing apparatus.

10 Claims, 12 Drawing Sheets

12

ULTRASOUND DIAGNOSTIC SYSTEM AND IMAGE PROCESSING APPARATUS

CROSS REFERENCE TO RELATED APPLICATION

The present application claims priority from Japanese Patent Application No. 2023-149571 filed on Sep. 14, 2023, the content of which is hereby incorporated by reference into this application.

BACKGROUND OF THE INVENTION

1. Field of the Invention

The present disclosure relates to an ultrasound diagnostic system and an image processing apparatus.

2. Description of the Related Art

In general, an ultrasound diagnostic apparatus acquires Raw data (for example, data to which processing for generating an ultrasound image for display is not applied) by transmitting and receiving ultrasonic waves, applies image processing to the Raw data to generate an ultrasound image, and displays the ultrasound image on a display.

JP2009-112357A discloses a device that generates an ultrasound image based on Raw data received from an ultrasound diagnostic apparatus.

SUMMARY OF THE INVENTION

For example, even in a case in which the ultrasound diagnostic apparatus itself can execute three-dimensional image processing (for example, image processing for a circulatory system) in real time, there are limitations to executing the three-dimensional image processing in real time by an external device (for example, a medical image diagnostic system) other than the ultrasound diagnostic apparatus. Therefore, it is difficult to observe or analyze the ultrasound image generated by the ultrasound diagnostic apparatus in real time at a remote location.

In addition, a person (for example, a doctor or a family member of a subject) who observes or analyzes an ultrasound image displayed on the external device does not necessarily want to observe or analyze the ultrasound image displayed on the ultrasound diagnostic apparatus. Accordingly, the needs of such a person cannot be met by simply transmitting the ultrasound image displayed on the ultrasound diagnostic apparatus to the external device and displaying the ultrasound image on the external device.

An object of the present disclosure is to provide an ultrasound image different from an ultrasound image displayed on an ultrasound diagnostic apparatus to a person in a remote location as close to real time as possible.

According to one aspect of the present disclosure, there is provided an ultrasound diagnostic system comprising: an ultrasound diagnostic apparatus; and an image processing apparatus, in which the ultrasound diagnostic apparatus includes an acquisition unit that acquires Raw data by transmitting and receiving ultrasonic waves, a first image processing unit that generates a first ultrasound image by applying first image processing to the Raw data, a first display controller that displays the first ultrasound image generated by the first image processing unit on a first display of the ultrasound diagnostic apparatus, and a first transmission unit that transmits the Raw data, to which the first image processing is not applied by the first image processing unit, to the image processing apparatus via a high-speed communication path, and the image processing apparatus includes a second reception unit that receives the Raw data transmitted by the first transmission unit via the high-speed communication path, a second image processing unit that generates a second ultrasound image different from the first ultrasound image displayed on the first display of the ultrasound diagnostic apparatus by applying second image processing different from the first image processing to the Raw data received by the second reception unit, and a second display controller that displays the second ultrasound image generated by the second image processing unit on a second display of the image processing apparatus.

The second image processing unit may generate a three-dimensional ultrasound image as the second ultrasound image based on the Raw data.

The image processing apparatus may further include a user interface that receives selection of the second image processing, the second image processing unit may generate the second ultrasound image by applying the second image processing to the Raw data in response to the selection received by the user interface, and the second display controller may display the second ultrasound image on the second display.

The image processing apparatus may further include a user interface that receives selection of the second image processing, and a second transmission unit that transmits control information indicating the selection received by the user interface to the ultrasound diagnostic apparatus via the high-speed communication path, the ultrasound diagnostic apparatus may further include a first reception unit that receives the control information transmitted by the second transmission unit via the high-speed communication path, the first image processing unit may generate a third ultrasound image by applying the second image processing indicated by the control information received by the first reception unit to the Raw data, and the first display controller may display the third ultrasound image on the first display.

The image processing apparatus may further include a user interface that receives selection of third image processing, and a second transmission unit that transmits control information indicating the selection received by the user interface to the ultrasound diagnostic apparatus via the high-speed communication path, the ultrasound diagnostic apparatus may further include a first reception unit that receives the control information transmitted by the second transmission unit via the high-speed communication path, the first image processing unit may generate a third ultrasound image by applying the third image processing indicated by the control information received by the first reception unit to the Raw data, and the first display controller may display the third ultrasound image on the first display.

The first transmission unit may transmit information indicating the first image processing to the image processing apparatus via the high-speed communication path, the second reception unit may receive the information indicating the first image processing transmitted by the first transmission unit via the high-speed communication path, the second image processing unit may generate the second ultrasound image by applying the second image processing to the Raw data and generates the first ultrasound image by applying the first image processing to the Raw data in accordance with the information indicating the first image processing, and the second display controller may display the second ultrasound image and the first ultrasound image side by side on the second display.

The first transmission unit may transmit header data including information indicating the first image processing to the image processing apparatus via the high-speed communication path in association with the Raw data, the second reception unit may receive the Raw data and the header data transmitted by the first transmission unit via the high-speed communication path, the second image processing unit may generate a fourth ultrasound image by applying the first image processing to the Raw data in accordance with the information indicating the first image processing included in the header data, and the second display controller may display the fourth ultrasound image on the second display.

The second display controller may display the second ultrasound image on the second display in accordance with a designated display mode, and displays mode identification information for identifying the display mode on the second display.

The display mode may be any one of a first mode in which the second ultrasound image generated by applying the second image processing to the Raw data while receiving the Raw data is displayed, a second mode in which the second ultrasound image generated by receiving the Raw data to be stored in a memory and applying the second image processing to the Raw data is displayed, or a third mode in which the second ultrasound image is displayed in a still state.

The ultrasound diagnostic apparatus may be used for circulatory organ examination, and the first image processing and the second image processing may be image processing related to the circulatory organ examination.

The ultrasound diagnostic apparatus may be used for obstetric examination, and the first image processing and the second image processing may be image processing related to the obstetric examination.

According to another aspect of the present disclosure, there is provided an image processing apparatus comprising: a second reception unit that receives Raw data, via a high-speed communication path, from an ultrasound diagnostic apparatus that acquires the Raw data through transmission and reception of ultrasonic waves and generates a first ultrasound image by applying first image processing to the Raw data; a second image processing unit that generates a second ultrasound image different from the first ultrasound image by applying second image processing different from the first image processing to the Raw data received by the second reception unit; and a second display controller that displays the second ultrasound image generated by the second image processing unit on a display.

According to the present disclosure, it is possible to provide an ultrasound image different from an ultrasound image displayed on an ultrasound diagnostic apparatus to a person in a remote location as close to real time as possible.

DESCRIPTION OF THE PREFERRED EMBODIMENTS

Figure 1:
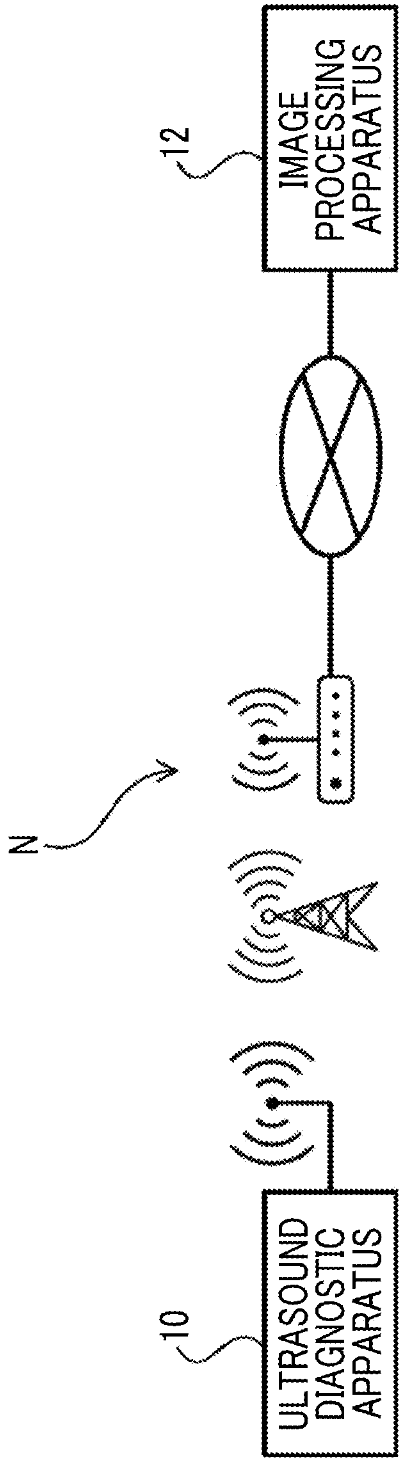
FIG. 1 is a diagram showing an example of a configuration of an ultrasound diagnostic system according to an embodiment.

An ultrasound diagnostic system according to an embodiment will be described with reference to FIG. 1. FIG. 1 is a block diagram showing a configuration of the ultrasound diagnostic system according to the embodiment.

The ultrasound diagnostic system includes an ultrasound diagnostic apparatus 10 and an image processing apparatus 12. The ultrasound diagnostic apparatus 10 and the image processing apparatus 12 have a function of communicating with each other via a communication path N.

The communication path N includes a high-speed communication path. For example, the high-speed communication path is a wireless communication path using a sixth generation mobile communication system (6G) or a wireless communication path using a next-generation communication system after 6G. A communication path through which data acquired by the ultrasound diagnostic apparatus 10 can be transmitted to the image processing apparatus 12 in real time may be used as the high-speed communication path. The communication path N may include a network such as the Internet or a local area network (LAN). A wired line may be used as a part of the communication path N.

The ultrasound diagnostic apparatus 10 transmits ultrasonic waves into a subject using an ultrasound probe and receives the ultrasonic waves reflected in the subject, thereby generating data representing an inside of the subject. Image processing is applied to the data to generate an ultrasound image representing a tissue or the like inside the subject.

The data generated by the ultrasound diagnostic apparatus 10 is transmitted to the image processing apparatus 12 via the communication path N. For example, in a case in which a transmission request of the data is transmitted from the image processing apparatus 12 to the ultrasound diagnostic apparatus 10, the data is transmitted from the ultrasound diagnostic apparatus 10 to the image processing apparatus 12 via the communication path N in response to the request.

The image processing apparatus 12 receives the data from the ultrasound diagnostic apparatus 10 via the communication path N. The image processing apparatus 12 generates an ultrasound image by applying image processing to the data. For example, the image processing apparatus 12 is a personal computer (hereinafter, referred to as "PC"), a tablet PC, a smartphone, a server, a mobile phone, or the like.

For example, the ultrasound diagnostic apparatus 10 generates Raw data by transmitting and receiving the ultrasonic waves. The Raw data is data to which image processing for generating an ultrasound image for display is not applied. The Raw data is transmitted from the ultrasound diagnostic apparatus 10 to the image processing apparatus 12. The image processing apparatus 12 generates an ultrasound image by applying image processing to the Raw data. For example, the ultrasound image is displayed on a display of the image processing apparatus 12.

For example, in a case in which a user of the image processing apparatus 12 issues an instruction to execute the image processing, the image processing apparatus 12 generates the ultrasound image by applying the image processing instructed by the user to the Raw data. For example, the image processing apparatus 12 executes image processing different from the image processing executed by the ultrasound diagnostic apparatus 10. Of course, the image processing apparatus 12 may execute the same image processing as the image processing executed by the ultrasound diagnostic apparatus 10.

Figure 2:
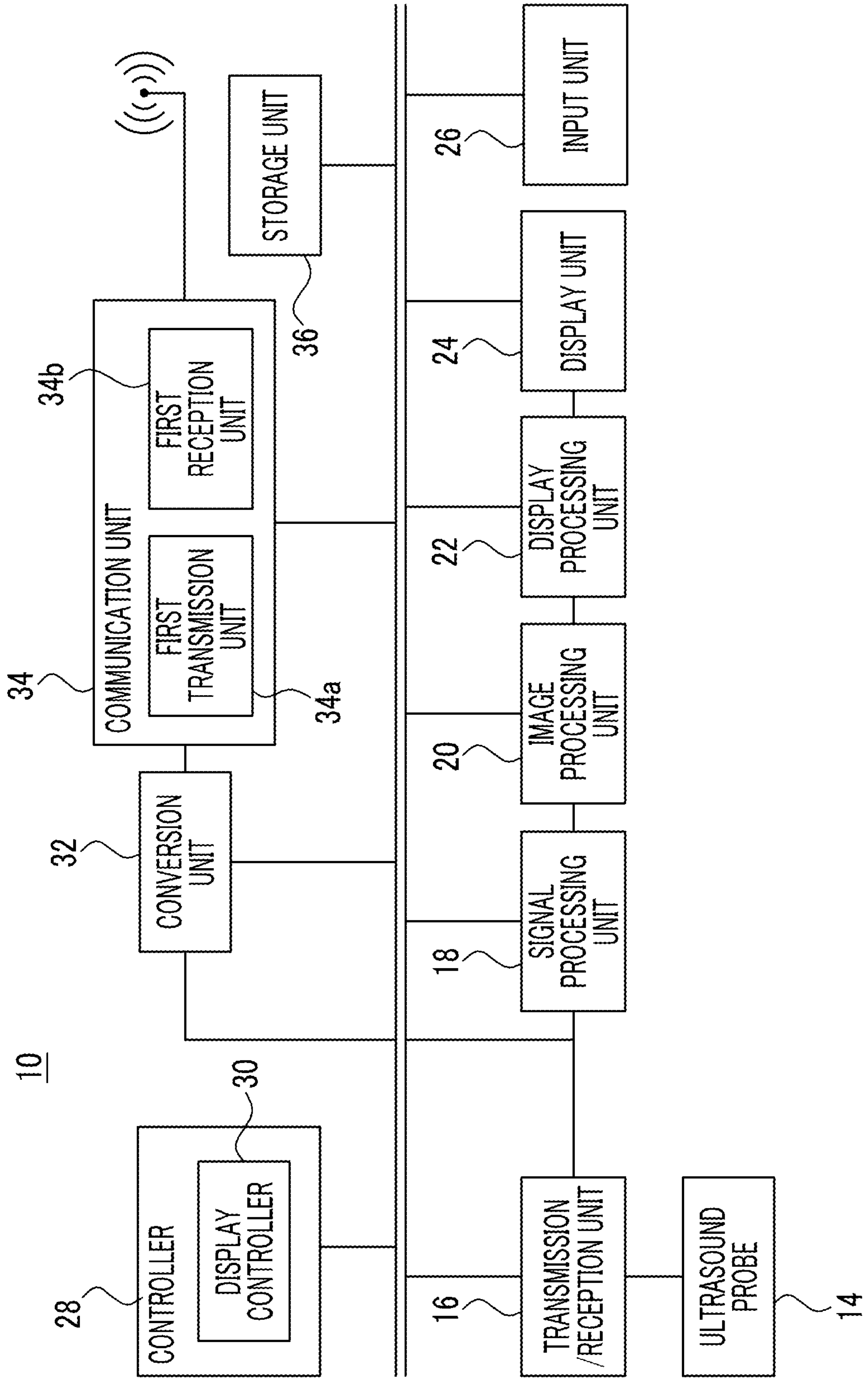
FIG. 2 is a diagram showing an example of a configuration of an ultrasound diagnostic apparatus according to the embodiment.

Hereinafter, a configuration of the ultrasound diagnostic apparatus 10 will be described with reference to FIG. 2. FIG. 2 is a block diagram showing an example of the configuration of the ultrasound diagnostic apparatus 10.

The ultrasound diagnostic apparatus 10 includes an ultrasound probe 14, a transmission/reception unit 16, a signal processing unit 18, an image processing unit 20, a display processing unit 22, a display unit 24, an input unit 26, a controller 28, a display controller 30, a conversion unit 32, a communication unit 34, and a storage unit 36.

The ultrasound probe 14 is a device that transmits and receives the ultrasonic waves. For example, the ultrasound probe 14 includes a 2D array transducer. The 2D array transducer is formed by two-dimensionally arranging a plurality of ultrasound transducers. An ultrasound beam is formed by the 2D array transducer. In a case in which electronic scanning with the ultrasound beam is repeatedly performed, a scanning surface as a two-dimensional echo data acquisition space is formed for each electronic scanning. In a case in which two-dimensional scanning with the ultrasound beam is performed, a three-dimensional space as a three-dimensional echo data acquisition space is formed. As a scanning method, sector scanning, linear scanning, convex scanning, or the like is used.

In the transmission, the transmission/reception unit 16 supplies a plurality of transmission signals having a certain delay relationship to the plurality of ultrasound transducers included in the ultrasound probe 14. As a result, a transmission beam of the ultrasonic waves is formed. In the reception, a reflected wave (RF signal) from a living body is received by the ultrasound probe 14. As a result, a plurality of reception signals are output from the ultrasound probe 14 to the transmission/reception unit 16. The transmission/reception unit 16 forms a reception beam by applying phasing addition processing to the plurality of reception signals. Data of the reception beam is output to the signal processing unit 18. That is, the transmission/reception unit 16 forms the reception beam by performing delay processing on the reception signal obtained from each ultrasound transducer in accordance with a delay processing condition for each ultrasound transducer and performing addition processing on the plurality of reception signals obtained from the plurality of ultrasound transducers. The delay processing condition is defined by reception delay data indicating a delay time. A reception delay data set (that is, a set of delay times) corresponding to the plurality of ultrasound transducers is supplied from the controller 28. The transmission/reception unit 16 functions as a transmission beam former and a reception beam former. For example, the transmission/reception unit 16 includes an A/D converter, a detector, an amplification circuit, and the like. The unit that transmits and receives the ultrasonic waves and the unit that realizes the beam former may be configured as separate units.

The signal processing unit 18 applies signal processing to the beam data output from the transmission/reception unit 16. For example, the signal processing includes detection and amplitude compression such as logarithmic compression. The data to which the signal processing is applied is output to the image processing unit 20.

The image processing unit 20 generates an ultrasound image by applying image processing to the data to which the signal processing is applied. For example, the image processing includes a coordinate transformation function and an interpolation processing function using a digital scan converter (DSC). For example, the ultrasound image is a B-mode image, a color Doppler image, a pulse Doppler image, a strain image, a shear wave elastography image, or the like. The ultrasound image may be a two-dimensional image or a three-dimensional image.

The display processing unit 22 generates a display image by overlaying necessary graphic data on the ultrasound image. The display image is output to the display unit 24. One or a plurality of images are arranged and displayed in a display aspect according to a display mode.

The display unit 24 is a display such as a liquid crystal display or an EL display. The ultrasound image such as the B-mode image is displayed on the display unit 24. The display unit 24 may be a device comprising a display and the input unit 26. For example, a graphic user interface (GUI) may be realized by the display unit 24. In addition, a user interface such as a touch panel may be realized by the display unit 24.

The input unit 26 is a device for the user to input various types of information (for example, a condition required for imaging, a command, and patient information) to the ultrasound diagnostic apparatus 10. For example, the input unit 26 is an operation panel, a switch, a button, a keyboard, a mouse, a track ball, a joystick, or the like.

The controller 28 controls an operation of each unit of the ultrasound diagnostic apparatus 10. The controller 28 includes the display controller 30.

The display controller 30 displays the ultrasound image on the display unit 24. The display controller 30 may display information or an image other than the ultrasound image on the display unit 24.

The conversion unit 32 converts the Raw data into transmission data. The Raw data is data transmitted from the ultrasound diagnostic apparatus 10 to the image processing apparatus 12. For example, the conversion unit 32 generates the transmission data by adding header data to the Raw data.

The Raw data is data to which processing for generating the ultrasound image for display is not applied. For example, data that is output from the transmission/reception unit 16 and to which the signal processing by the signal processing unit 18 is not applied is the Raw data. In this case, the transmission/reception unit 16 corresponds to an example of an acquisition unit. Data to which the signal processing by the signal processing unit 18 is applied may be the Raw data. That is, data that is output from the signal processing unit 18 and to which the image processing by the image processing unit 20 is not applied may be the Raw data. In this case, the signal processing unit 18 corresponds to an example of an acquisition unit.

The header data is metadata (that is, accessory information) added to the Raw data. For example, the header data includes information on an imaging mode, information on the Raw data, scan information, signal processing information, image processing information, measurement information, frame information, patient information, and the like. The imaging mode is an imaging mode executed by the ultrasound diagnostic apparatus 10 in order to acquire the Raw data. For example, the imaging mode is a B mode (THI), an M mode, a PW mode, a CW mode, a CFI mode, a CFA mode, a TE mode, an SWE mode, or the like. The information on the Raw data includes a data length, the number of samples, an interval, a size, an address, a data type (rectangular coordinate IQ or polar coordinate rΘ), and the like. The scan information includes the number of lines, an interval, a size, an address, a type (Lin, Sec, or Conv), and the like. The signal processing information is information indicating the signal processing by the signal processing unit 18. The signal processing information includes information on a gain, a filter, or the like. The image processing information is information indicating the image processing by the image processing unit 20. The image processing information includes information on a region of interest (ROI), a filter, or the like. The measurement information includes a parameter related to the measurement executed by the ultrasound diagnostic apparatus 10, and the like. The frame information is information indicating a size, a position, or the like of the ultrasound image. The patient information is information indicating an ID, a gender, an age, or the like of a patient from whom the Raw data is acquired. For example, in a case in which the imaging is performed by the ultrasound diagnostic apparatus 10, each information included in the header data is input to the ultrasound diagnostic apparatus 10 by the user, such as an examination technician or a doctor, or is input to the ultrasound diagnostic apparatus 10 from an external device, such as a server. Information other than the above-described information may be included in the header data. The user may designate the information included in the header data.

The communication unit 34 is a communication interface. The communication unit 34 has a first transmission unit 34*a* that transmits data to the external device, and a first reception unit 34*b* that receives data. The first transmission unit 34*a* transmits the transmission data to the image processing apparatus 12 via the communication path N. As a result, the Raw data is transmitted from the ultrasound diagnostic apparatus 10 to the image processing apparatus 12. The first reception unit 34*b* receives the information transmitted from the image processing apparatus 12 via the communication path N. For example, as described below, control information indicating second image processing or third image processing selected by the user is transmitted from the image processing apparatus 12 to the ultrasound diagnostic apparatus 10 via the communication path N. The first reception unit 34*b* receives the control information.

The storage unit 36 constitutes one or a plurality of storage regions for storing data. For example, the storage unit 36 is a hard disk drive (HDD), a solid state drive (SSD), various memories (for example, RAM, DRAM, or ROM), other storage devices (for example, optical disk), or a combination thereof. For example, the storage unit 36 stores Raw data, ultrasound image data, information indicating imaging conditions, patient information, and the like. The header data or the transmission data may be stored in the storage unit 36.

The image processing unit 20 corresponds to an example of a first image processing unit. The image processing by the image processing unit 20 corresponds to an example of first image processing. The ultrasound image generated by applying the first image processing to the Raw data corresponds to an example of a first ultrasound image. The display of the display unit 24 corresponds to an example of a first display. The display controller 30 corresponds to an example of a first display controller.

Figure 3:
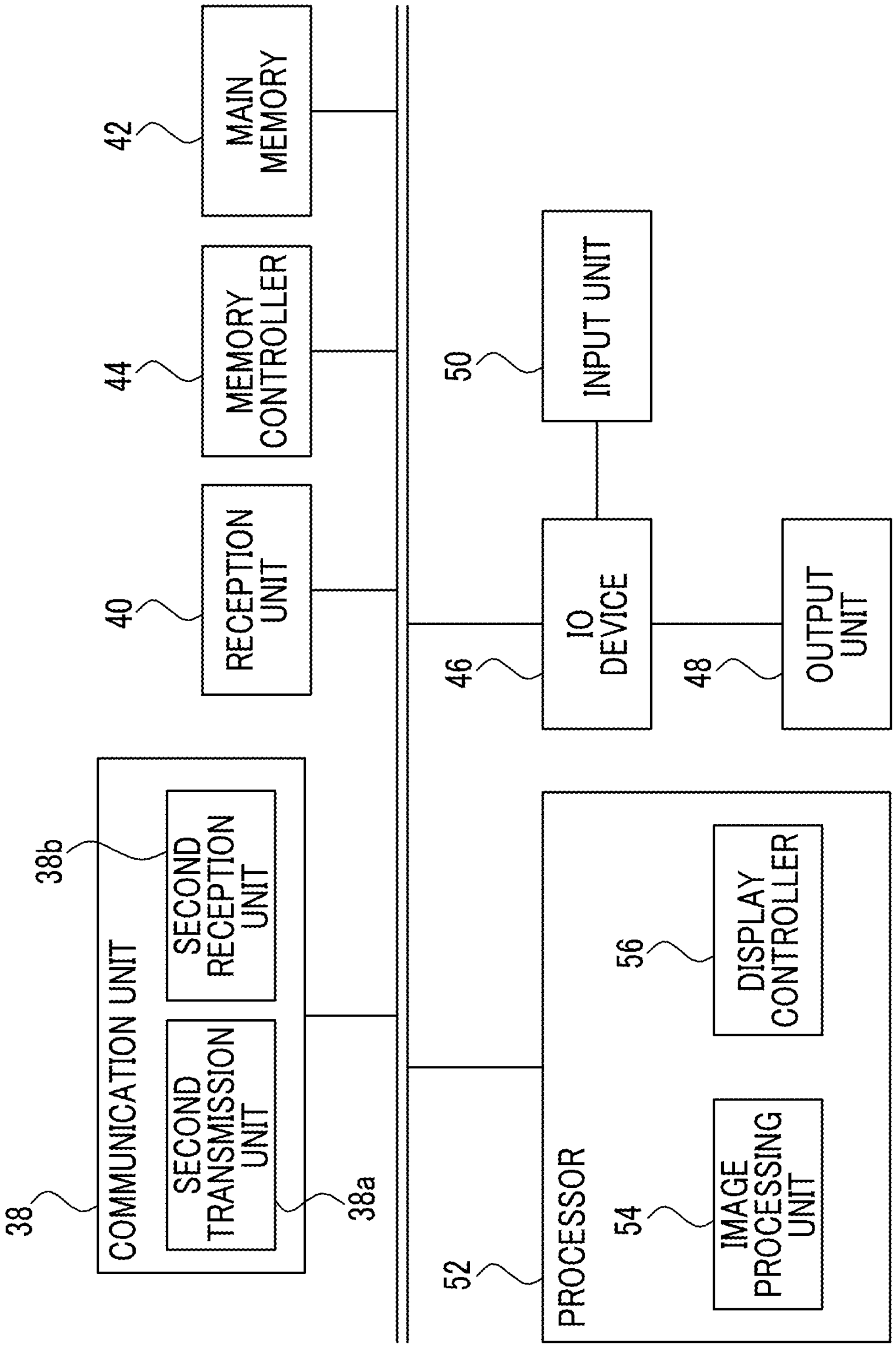
FIG. 3 is a diagram showing an example of a configuration of an image processing apparatus according to the embodiment.

Hereinafter, a configuration of the image processing apparatus 12 will be described with reference to FIG. 3. FIG. 3 is a diagram showing an example of the configuration of the image processing apparatus 12.

The image processing apparatus 12 includes a communication unit 38, a reception unit 40, a main memory 42, a memory controller 44, an IO device 46, an output unit 48, an input unit 50, and a processor 52.

The communication unit 38 is a communication interface. The communication unit 38 has a second transmission unit 38*a* that transmits data to the external device, and a second reception unit 38*b* that receives data. For example, the second transmission unit 38*a* transmits control information indicating the second image processing or the third image processing selected by the user to the ultrasound diagnostic apparatus 10 via the communication path N. The second reception unit 38*b* receives the transmission data transmitted from the ultrasound diagnostic apparatus 10 via the communication path N. As a result, the second reception unit 38*b* receives the Raw data.

The reception unit 40 receives the transmission data received by the communication unit 38 and executes a process of storing the transmission data in the main memory 42.

The main memory 42 constitutes one or a plurality of storage regions for storing data. The main memory 42 is, for example, a hard disk drive (HDD), a solid state drive (SSD), various memories (for example, RAM, DRAM, or ROM), other storage devices (for example, optical disk), or a combination thereof. For example, the transmission data is stored in the main memory 42. The Raw data and the header data may be separately stored in the main memory 42. The other information may be stored in the main memory 42.

The memory controller 44 controls the main memory 42. For example, the memory controller 44 stores the transmission data received by the reception unit 40 in the main memory 42. In addition, the memory controller 44 controls the reading of the data from the main memory 42.

The IO device 46 is connected to the output unit 48 and the input unit 50. For example, various types of information are output to the output unit 48 via the IO device 46 and are input to the image processing apparatus 12 from the input unit 50 via the IO device 46.

The output unit 48 includes a display unit. The display unit is a display such as a liquid crystal display or an EL display. The display unit may be a device comprising a display and the input unit 50. For example, a graphic user interface (GUI) may be realized by the display unit. In addition, a user interface such as a touch panel may be realized by the display unit. The output unit 48 may include a speaker.

The input unit 50 is a device for the user to input various types of information to the image processing apparatus 12. For example, the input unit 50 is an operation panel, a switch, a button, a keyboard, a mouse, a track ball, a joystick, or the like.

The processor 52 includes a controller, an operation unit, a cache, a bus I/F, and the like. The controller controls the image processing apparatus 12. The operation unit performs various operations. In addition, the processor 52 includes an image processing unit 54 and a display controller 56.

The image processing unit 54 generates an ultrasound image by applying image processing to the Raw data. The image processing may include the signal processing described above.

The display controller 56 displays the ultrasound image on a display of the output unit 48. The display controller 56 may display information or an image other than the ultrasound image on the display of the output unit 48.

The image processing unit 54 corresponds to an example of a second image processing unit. The image processing by the image processing unit 54 corresponds to an example of second image processing. The ultrasound image generated by applying the second image processing to the Raw data corresponds to an example of a second ultrasound image. The display of the output unit 48 corresponds to an example of a second display. The display controller 56 corresponds to an example of a second display controller.

In addition, the image processing apparatus 12 includes a user interface that receives selection of the second image processing. The user interface is realized by the output unit 48 and the input unit 50. The display controller 56 displays a screen for selecting the second image processing on the display of the output unit 48. For example, a list of a plurality of different second image processing is displayed on the screen. The user can select the second image processing on the screen by operating the input unit 50. Of course, the second image processing may be selected by voice. A cross section or a diagnosis site to be displayed may be designated by the user interface. The image processing unit 54 generates a second ultrasound image by applying the second image processing to the Raw data in accordance with the selection received by the user interface. The display controller 56 displays the second ultrasound image on the display of the output unit 48.

The second transmission unit **38*a* may transmit the control information indicating the selection received by the user interface to the ultrasound diagnostic apparatus 10 via the communication path N. That is, in a case in which the second image processing is selected by the user on the screen, the second transmission unit 38*a* transmits the control information indicating the second image processing selected by the user to the ultrasound diagnostic apparatus 10 via the communication path N. Similarly, in a case in which the second image processing is selected by voice, the second transmission unit 38*a* transmits the control information indicating the selected second image processing to the ultrasound diagnostic apparatus 10**.

The first reception unit **34*b* of the ultrasound diagnostic apparatus 10 receives the control information transmitted by the second transmission unit 38*a* of the image processing apparatus 12 via the communication path N. The image processing unit 20 of the ultrasound diagnostic apparatus 10 generates a third ultrasound image by applying the second image processing indicated by the control information received by the first reception unit 34*b* to the Raw data. The display controller 30 of the ultrasound diagnostic apparatus 10 displays the third ultrasound image on the display of the display unit 24**.

Figure 4:
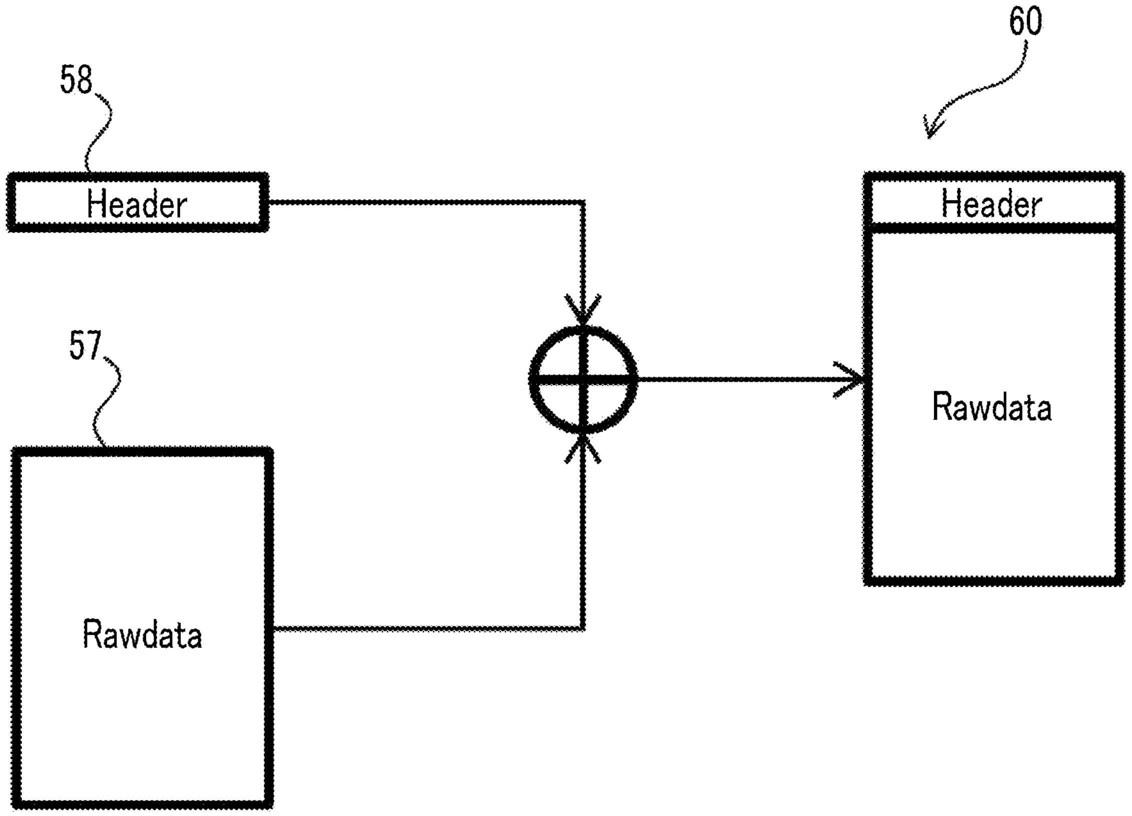
FIG. 4 is a diagram showing an example of a structure of transmission data.

Hereinafter, a structure of the transmission data will be described with reference to FIG. 4. FIG. 4 shows an example of the structure of the transmission data.

The ultrasound diagnostic apparatus 10 generates Raw data 57 by transmitting and receiving the ultrasonic waves. The conversion unit 32 generates transmission data 60 by adding header data 58 to the Raw data 57. The transmission data 60 is transmitted from the ultrasound diagnostic apparatus 10 to the image processing apparatus 12.

Figure 5:
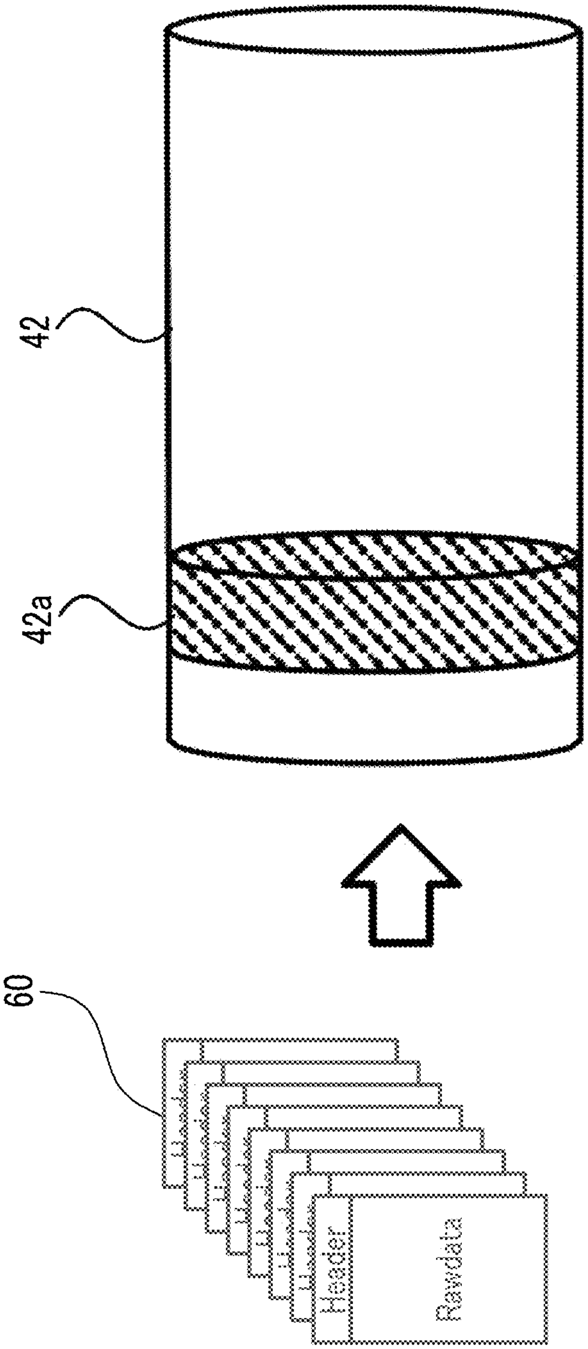
FIG. 5 is a diagram showing data and a main memory.

For example, as shown in FIG. 5, the transmission data 60 is stored in the main memory 42 of the image processing apparatus 12. A storage region **42*a* for the Raw data is shown in FIG. 5**.

Figure 6:
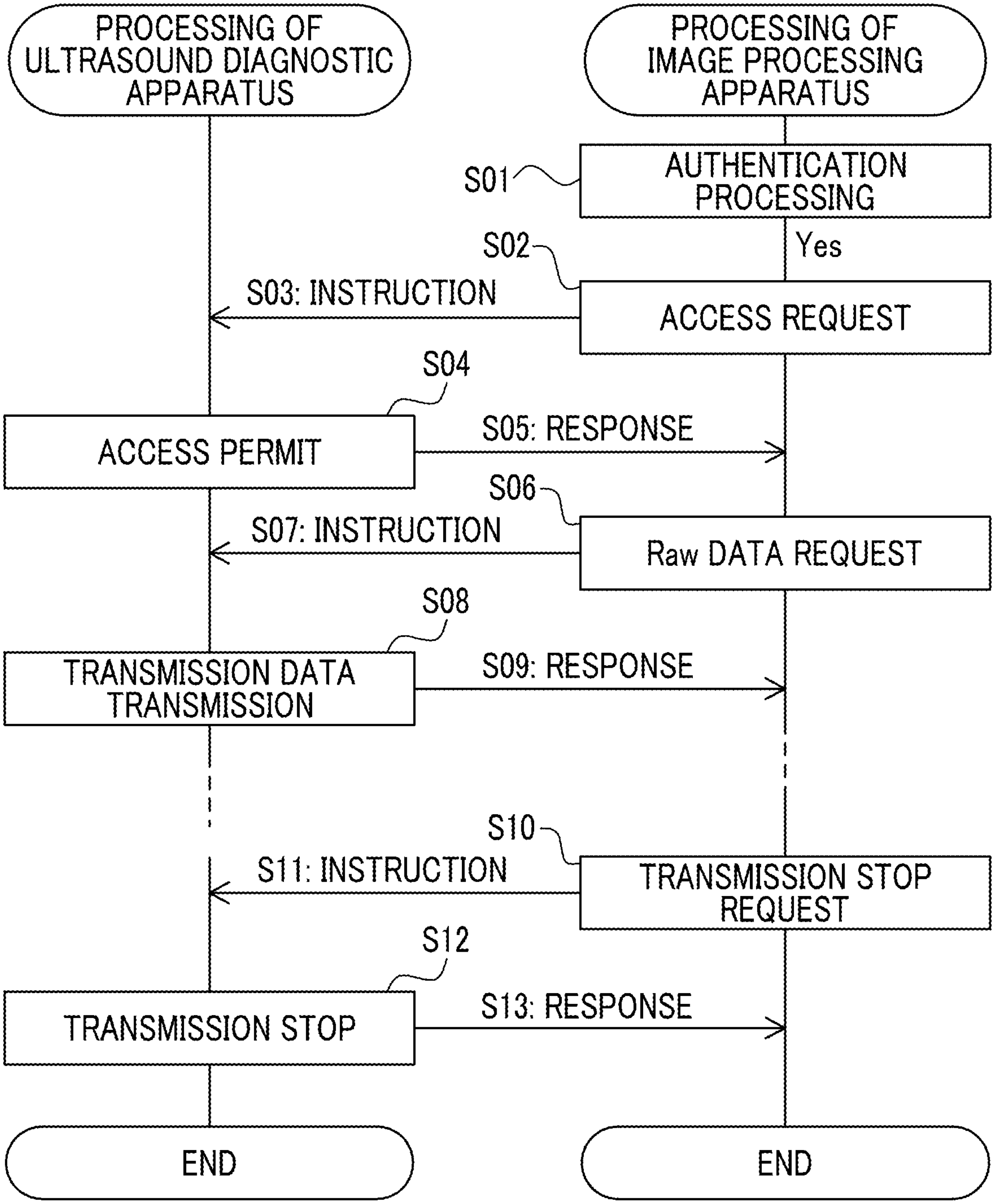
FIG. 6 is a diagram showing an example of processing by the ultrasound diagnostic system.

Hereinafter, a flow of processing by the ultrasound diagnostic system will be described with reference to FIG. 6. FIG. 6 shows a flowchart showing the flow of processing by the ultrasound diagnostic system.

First, user authentication is performed by the image processing apparatus 12 (S01). For example, the user authentication is performed using personal information, such as a password, a face, or a fingerprint, registered in advance in the image processing apparatus 12. In a case in which the authentication is successful, the processes of step S02 and subsequent steps are executed. In a case in which the authentication fails, the processes of step S02 and subsequent steps are not executed. The user authentication does not need to be performed. In this case, the process of step S01 is not performed, and the processes of step S02 and subsequent steps are executed. Hereinafter, the processes of step S02 and subsequent steps will be described.

For example, an instruction screen is displayed on the display of the image processing apparatus 12. In a case in which the user requests access to the ultrasound diagnostic apparatus 10 on the instruction screen (S02), the image processing apparatus 12 issues an instruction to access the ultrasound diagnostic apparatus 10 (S03).

In a case in which the instruction for the access is received, the ultrasound diagnostic apparatus 10 permits the access to the ultrasound diagnostic apparatus 10 (S04) and transmits a response corresponding to the instruction to the image processing apparatus 12 (S05). The ultrasound diagnostic apparatus 10 may determine whether or not to permit the access by using the personal information of the user (for example, the personal information input to the image processing apparatus 12).

In a case in which the response is received from the ultrasound diagnostic apparatus 10, the image processing apparatus 12 requests the ultrasound diagnostic apparatus 10 to transmit the Raw data (S06). The image processing apparatus 12 instructs the ultrasound diagnostic apparatus 10 to transmit the Raw data (S07).

In a case in which the instruction to transmit the Raw data is received, the ultrasound diagnostic apparatus 10 transmits the transmission data including the Raw data and the header data to the image processing apparatus 12 (S08). For example, the ultrasound diagnostic apparatus 10 includes the Raw data being currently acquired by the ultrasound diagnostic apparatus 10 in the transmission data, and transmits the transmission data to the image processing apparatus 12. The transmission data is transmitted to the image processing apparatus 12 as a response to the instruction to transmit the Raw data (S09). As a result, the transmission data including the Raw data is transmitted from the ultrasound diagnostic apparatus 10 to the image processing apparatus 12 in real time. The Raw data is stored in the main memory 42 of the image processing apparatus 12. In addition, the image processing apparatus 12 generates an ultrasound image by executing the image processing on the Raw data. The ultrasound image is displayed on the display of the image processing apparatus 12.

After that, in a case in which the user requests the image processing apparatus 12 to stop the transmission of the Raw data (S10), the image processing apparatus 12 instructs the ultrasound diagnostic apparatus 10 to stop the transmission (S11).

In a case in which the instruction to stop the transmission is received, the ultrasound diagnostic apparatus 10 stops the transmission of the transmission data (S12). As a result, the transmission data is not transmitted from the ultrasound diagnostic apparatus 10 to the image processing apparatus 12. A response to the transmission stop is transmitted from the ultrasound diagnostic apparatus 10 to the image processing apparatus 12 (S13).

Figure 7:
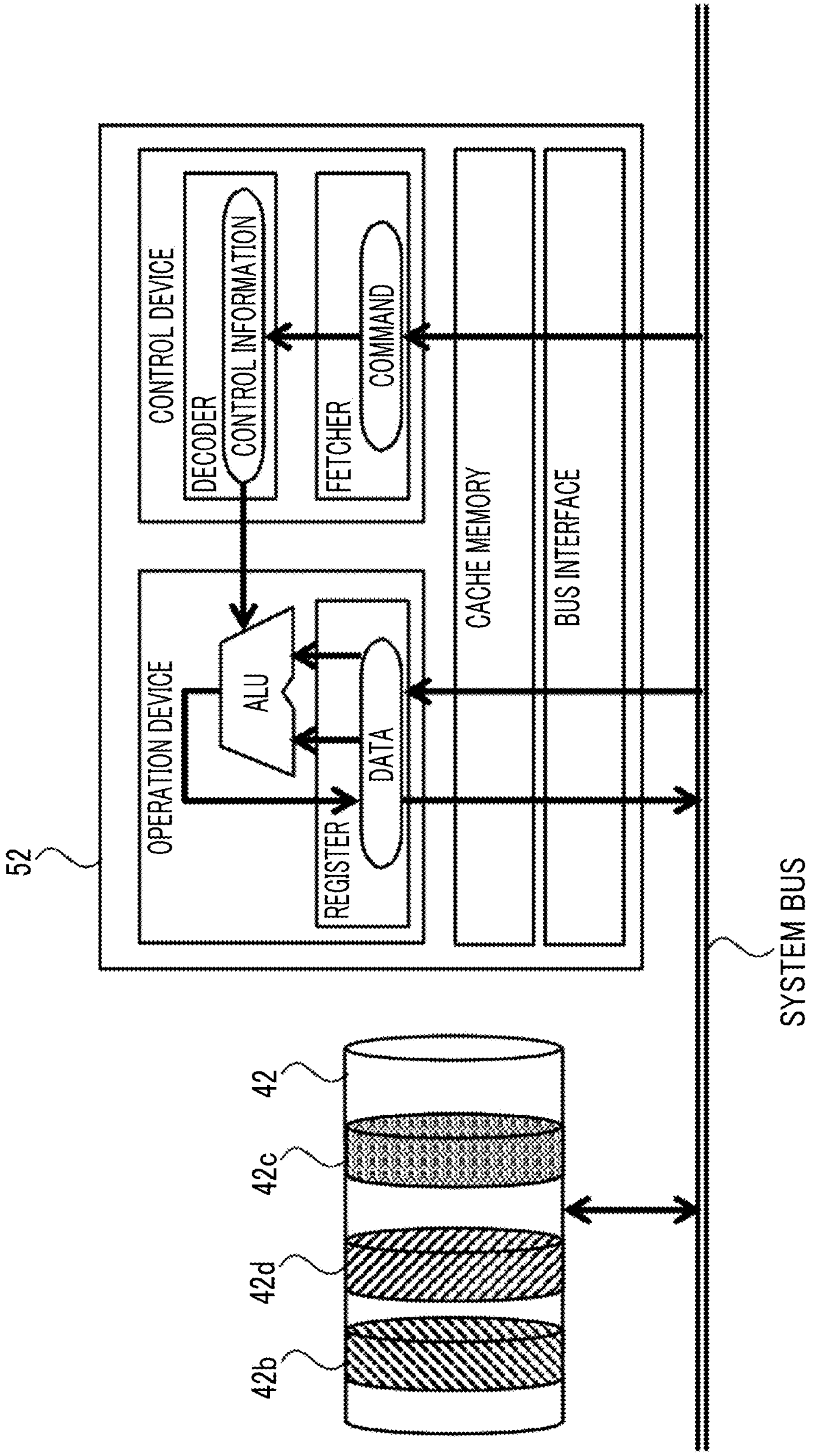
FIG. 7 is a diagram showing an example of processing by a processor of the image processing apparatus.

Hereinafter, processing by the processor 52 of the image processing apparatus 12 will be described with reference to FIG. 7.

In a case in which the transmission data is transmitted from the ultrasound diagnostic apparatus 10 to the image processing apparatus 12, the Raw data and the header data are stored in a storage region 42*b* of the main memory 42. A command for the image processing is stored in a storage region 42*c* of the main memory 42. For example, the command for the image processing is input to the image processing apparatus 12 via the input unit 50 and stored in the main memory 42, or is input to the image processing apparatus 12 via the communication unit 38 and stored in the main memory 42.

For example, the processor 52 includes a bus interface, a cache memory, a control device, and an operation device. The control device includes a fetcher and a decoder. The operation device includes an arithmetic logic unit (ALU) and a register.

The command stored in the storage region 42*c* is output to the fetcher via a system bus, a bus interface, and a cache memory, and is converted into control information by the decoder. The control information is output to the ALU. The Raw data stored in the storage region 42*b* is output to the register via the system bus, the bus interface, and the cache memory, and is output to the ALU from the register. The ALU performs an operation on the Raw data based on the control information. The ALU outputs result data generated by the operation to the main memory 42 via the register, the cache memory, the bus interface, and the system bus. The result data is stored in a storage region 42*d* of the main memory 42. For example, the result data is ultrasound image data.

In the present embodiment, the image processing unit 20 of the ultrasound diagnostic apparatus 10 generates a first ultrasound image by applying the first image processing to the Raw data. The display controller 30 displays the first ultrasound image on the display unit 24. The transmission data including the Raw data and the header data is transmitted from the ultrasound diagnostic apparatus 10 to the image processing apparatus 12 via the communication path N. The processor 52 of the image processing apparatus 12 generates a second ultrasound image different from the first ultrasound image by applying second image processing different from the first image processing to the Raw data. The processor 52 displays the second ultrasound image on the display of the output unit 48. Since the Raw data is transmitted from the ultrasound diagnostic apparatus 10 to the image processing apparatus 12 via the communication path N including the high-speed communication path, the second ultrasound image can be displayed on the display of the image processing apparatus 12 in real time or substantially in real time. That is, a time from the acquisition of the Raw data by the ultrasound diagnostic apparatus 10 to the display of the second ultrasound image on the display of the image processing apparatus 12 is shorter than in a case in which the high-speed communication path is not used. As a result, the second ultrasound image can be displayed on the display of the image processing apparatus 12 in real time or substantially in real time.

Figure 8:
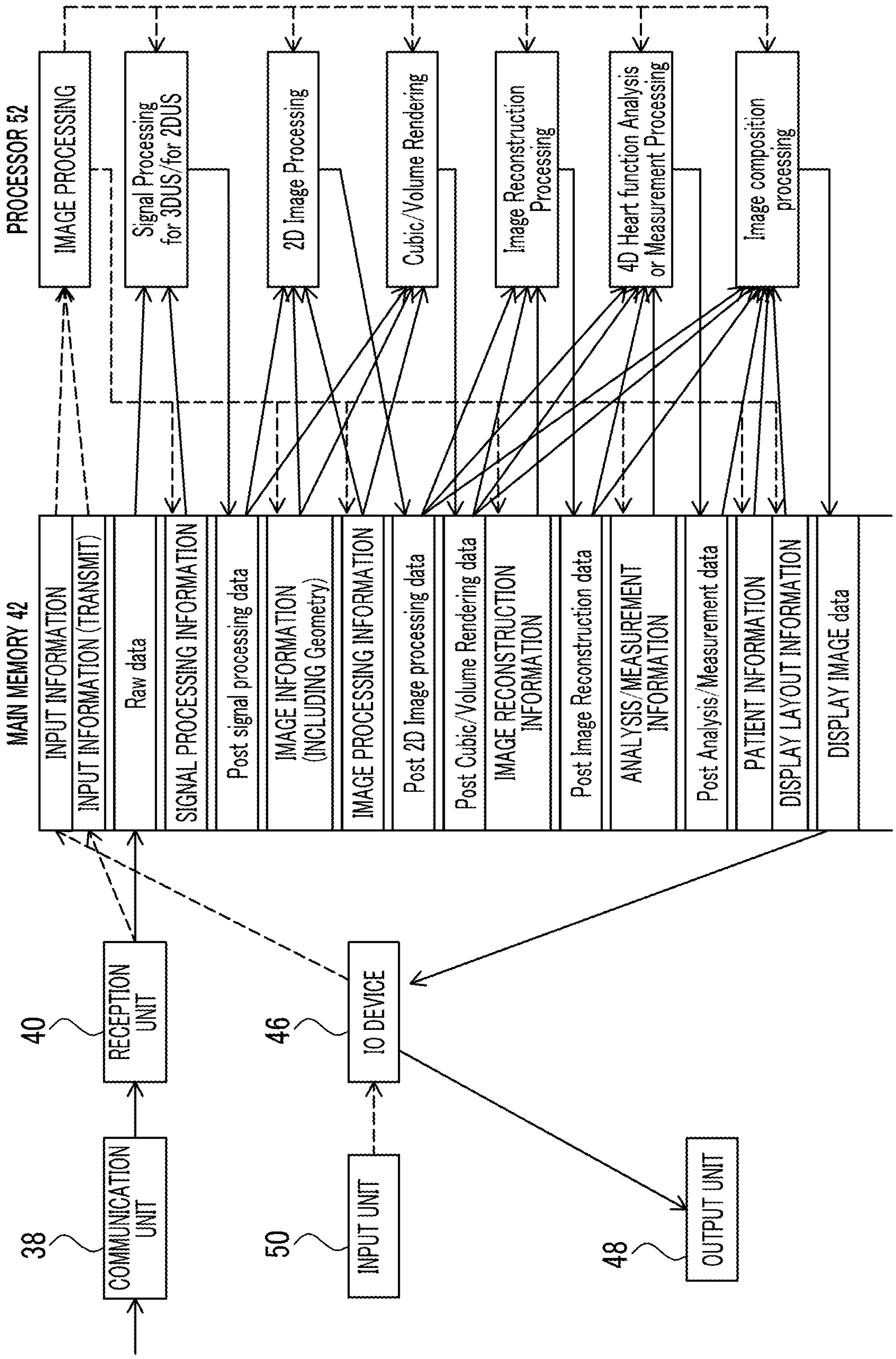
FIG. 8 is a diagram showing an example of processing by the processor of the image processing apparatus.

Hereinafter, a specific example of the image processing executed by the processor 52 will be described with reference to FIG. 8. In FIG. 8, a solid line indicates a flow of signal data (for example, Raw data), and a broken line indicates a flow of control data.

In a case in which the transmission data is transmitted from the ultrasound diagnostic apparatus 10 to the image processing apparatus 12, the communication unit 38 receives the transmission data. The reception unit 40 receives the transmission data from the communication unit 38 and stores the Raw data and the header data in the main memory 42. In a case in which the Raw data is compressed, the reception unit 40 develops (expands) the compressed data. The reception unit 40 may convert a format of the Raw data.

The input information (transmit) shown in FIG. 8 is information transmitted from the ultrasound diagnostic apparatus 10 to the image processing apparatus 12. The input information (transmit) may be included in the header data, or may be transmitted from the ultrasound diagnostic apparatus 10 to the image processing apparatus 12 separately from the header data. The input information (transmit) is received by the communication unit 38 and is stored in the main memory 42 by the reception unit 40. For example, the input information (transmit) includes information indicating the first image processing executed on the Raw data by the ultrasound diagnostic apparatus 10, patient information, and the like.

In addition, the input information is stored in the main memory 42. For example, the input information includes information indicating the second image processing, and the like. The input information is input to the image processing apparatus 12 from the input unit 50 of the image processing apparatus 12 via the IO device 46 and is stored in the main memory 42. The input information may be received by the communication unit 38 and input to the image processing apparatus 12.

For example, the processor 52 executes, on the raw data, signal processing for 3DUS/2DUS, 2D image processing, cubic/volume rendering, image reconstruction processing, 4D heart function analysis (or measurement processing), analysis/measurement, and image composition processing. These kinds of processing are examples, and only a part of these kinds of processing may be executed. For example, 4D heart function analysis or the like does not need to be executed.

The processor 52 reads the Raw data from the main memory 42 and applies the signal processing indicated by the signal processing information to the Raw data [signal processing for 3DUS/2DUS (three-dimensional ultrasound/two-dimensional ultrasound)]. As a result, post signal processing data is generated and stored in the main memory 42.

In a case in which the processor 52 reads the post signal processing data, the image information, and the image processing information from the main memory 42 and applies two-dimensional image processing to the post signal processing data (2D image processing), post 2D image processing data is generated and stored in the main memory 42. The image information includes geometric information and three-dimensional structure information.

In a case in which the processor 52 reads the post signal processing data, the image information, and the image processing information from the main memory 42 and applies three-dimensional rendering processing to the post signal processing data (cubic/volume rendering), post cubic/volume rendering data is generated and stored in the main memory 42.

In a case in which the processor 52 reads the post 2D image processing data, the post cubic/volume rendering data, and the image reconstruction information from the main memory 42 and executes the reconstruction processing (image reconstruction processing), post image reconstruction data is generated and stored in the main memory 42.

In a case in which the processor 52 reads the post 2D image processing data, the post cubic/volume rendering data, the post image reconstruction data, and the analysis/measurement information from the main memory 42 and executes the analysis processing (4D heart function analysis (or measurement processing)), post analysis/measurement data is generated and stored in the main memory 42.

In a case in which the processor 52 reads the post 2D image processing data, the post cubic/volume rendering data, the post image reconstruction data, the post analysis/measurement data, the patient information, and the display layout information from the main memory 42 and executes the composition processing (image composition processing), display image data is generated and stored in the main memory 42. The display image data is output to the output unit 48 via the IO device 46 and displayed on the display of the output unit 48. Data to be combined may be selected by the user, and the data selected by the user may be combined.

For example, in a case in which information included in the input information (transmit) is used as the signal processing information, the image information, the image processing information, the image reconstruction information, the analysis/measurement information, the patient information, and the display layout information, the first ultrasound image displayed by the ultrasound diagnostic apparatus 10 is generated. For example, the first ultrasound image is displayed on the display of the output unit 48.

In a case in which information included in the input information input via the IO device 46 is used as the signal processing information, the image information, the image processing information, the image reconstruction information, the analysis/measurement information, the patient information, and the display layout information, the second ultrasound image is generated. For example, the second ultrasound image is displayed on the display of the output unit 48.

The processing shown in FIG. 8 is merely an example, and the processing to be executed is changed depending on, for example, the diagnosis site, the analysis, the measurement, the patient, the medical department, or the like.

Hereinafter, specific examples of the first ultrasound image and the second ultrasound image will be described.

Figure 9:
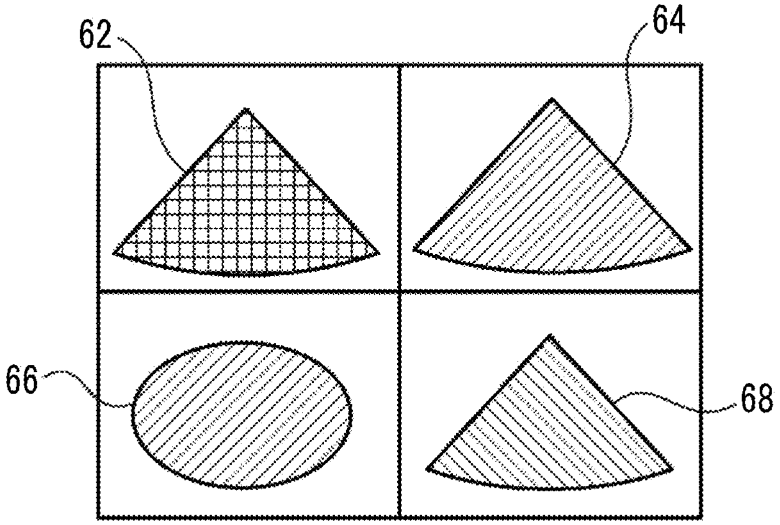
FIG. 9 is a diagram showing a display example of a first ultrasound image.

The first ultrasound image will be described with reference to FIG. 9. FIG. 9 shows the first ultrasound image. Here, as an example, ultrasound examination is performed on a circulatory organ.

Ultrasound images 62, 64, 66, and 68 are each the first ultrasound image, and are displayed on the display unit 24 of the ultrasound diagnostic apparatus 10. The ultrasound images 62, 64, 66, and 68 are images constituting a CV-3D image representing a blood vessel of the heart. CV is an abbreviation for cardiovascular. The 3D image is a three-dimensional ultrasound image, and is an image representing a tissue in a three-dimensional manner. For example, the ultrasound images 62, 64, 66, and 68 are images representing ventricles, atria, valves, and the like.

For example, a 2D array probe including a 2D array transducer is used as the ultrasound probe 14. The ultrasound diagnostic apparatus 10 acquires 4D data representing the heart by scanning a three-dimensional space including the heart with ultrasonic waves using the 2D array probe. The 4D data is an example of the Raw data and is data representing movement of a tissue in the three-dimensional space in a time series. That is, the 4D data is data representing a state in which a three-dimensional tissue is moving.

The image processing unit 20 of the ultrasound diagnostic apparatus 10 generates the ultrasound images 62, 64, 66, and 68 representing the heart (for example, the ventricles, the atria, and the valves) in a dynamic manner by applying first image processing (for example, image processing for generating the CV-3D image) to the 4D data. The display controller 30 displays the ultrasound images 62, 64, 66, and 68 on the display unit 24. The user (for example, an examination technician) of the ultrasound diagnostic apparatus 10 can observe or diagnose movement of the heart by referring to the ultrasound images 62, 64, 66, and 68. For example, the ultrasound images 62, 64, 66, and 68 are displayed on the display unit 24 in real time.

The ultrasound diagnostic apparatus 10 may acquire flow data representing blood flow. In this case, a 4D image representing the blood flow is generated by the image processing unit 20 and displayed on the display unit 24. The 4D image is an image showing a state in which a three-dimensional tissue is moving. That is, it can be said that the 4D image is a three-dimensional video image.

The 4D data as the Raw data is transmitted from the ultrasound diagnostic apparatus 10 to the image processing apparatus 12 via the communication path N with the header data added. The image processing unit 54 of the image processing apparatus 12 generates the second ultrasound image by applying the second image processing to the 4D data. The display controller 56 displays the second ultrasound image on the display of the output unit 48. In addition, the information indicating the first image processing is transmitted from the ultrasound diagnostic apparatus 10 to the image processing apparatus 12 via the communication path N. The information indicating the first image processing may be included in the header data and transmitted from the ultrasound diagnostic apparatus 10 to the image processing apparatus 12, or may be transmitted from the ultrasound diagnostic apparatus 10 to the image processing apparatus 12 as data separate from the header data.

Figure 10:
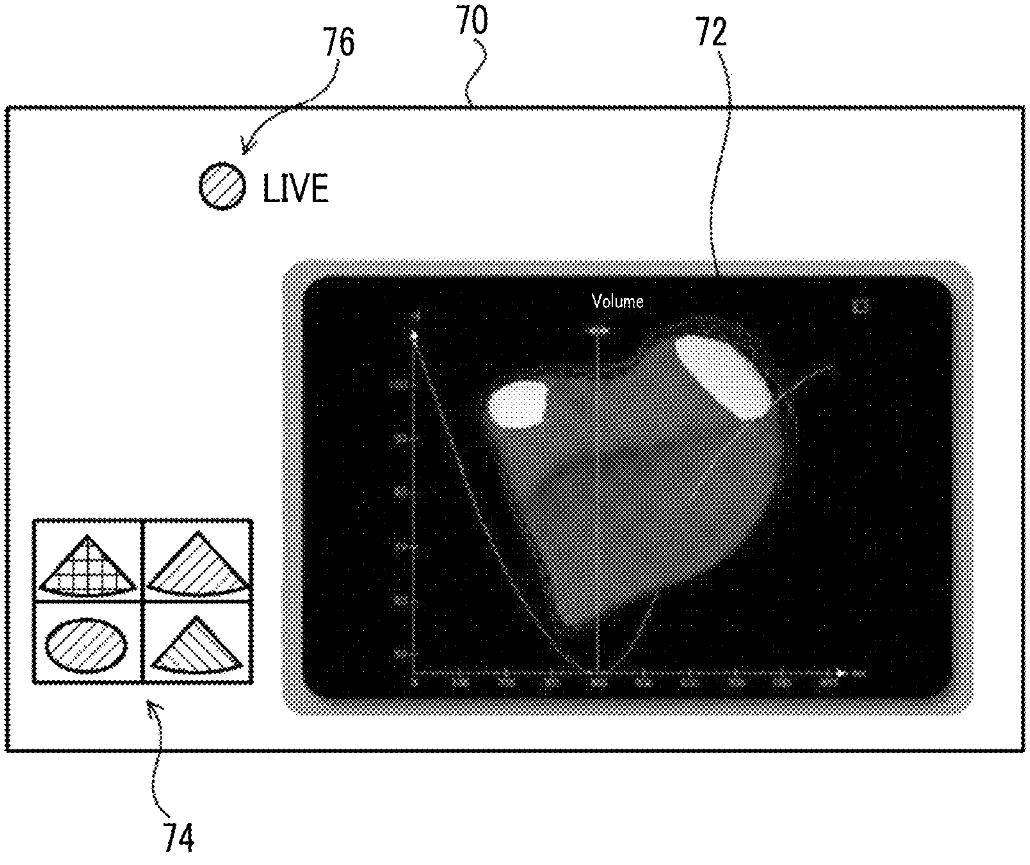
FIG. 10 is a diagram showing a display example of a second ultrasound image.

The second ultrasound image will be described with reference to FIG. 10. FIG. 10 shows the second ultrasound image.

A screen 70 is displayed on the display of the output unit 48 of the image processing apparatus 12. An ultrasound image 72 is the second ultrasound image and is displayed on the screen 70. The image processing unit 54 generates the ultrasound image 72 by applying the second image processing to the above-described 4D data. The second image processing is image processing different from the first image processing. The ultrasound image 72 is an ultrasound image different from the ultrasound images 62, 64, 66, and 68 displayed on the display of the ultrasound diagnostic apparatus 10. The ultrasound image 72 is an example of a CV-4D image (that is, an image showing a state in which a three-dimensional tissue is moving). For example, the image processing unit 54 generates the ultrasound image 72 by applying image processing for cardiac function analysis to the 4D data. The display controller 56 displays the ultrasound image 72 on the screen 70. For example, in a case in which the user (for example, a doctor) of the image processing apparatus 12 issues an instruction to execute the cardiac function analysis, the image processing unit 54 generates the ultrasound image 72 by applying the image processing for cardiac function analysis to the 4D data.

In the example shown in FIG. 10, an ultrasound image group 74 is displayed on the screen 70. The ultrasound image group 74 includes a plurality of first ultrasound images. For example, the ultrasound image group 74 includes the ultrasound images 62, 64, 66, and 68 described above. As described above, the information indicating the first image processing for generating the ultrasound images 62, 64, 66, and 68 is transmitted from the ultrasound diagnostic apparatus 10 to the image processing apparatus 12. The image processing unit 54 generates the ultrasound images 62, 64, 66, and 68 by applying the first image processing to the above-described 4D data. As a result, the ultrasound images 62, 64, 66, and 68 displayed on the display of the ultrasound diagnostic apparatus 10 can be reproduced by the image processing apparatus 12. That is, even in a case in which the ultrasound images 62, 64, 66, and 68 themselves are not transmitted from the ultrasound diagnostic apparatus 10 to the image processing apparatus 12, the Raw data and the information indicating the first image processing are transmitted from the ultrasound diagnostic apparatus 10 to the image processing apparatus 12, so that the ultrasound images 62, 64, 66, and 68 can be reproduced by the image processing apparatus 12. The display controller 56 displays the ultrasound image group 74 including the ultrasound images 62, 64, 66, and 68 on the screen 70.

For example, the information indicating the first image processing is included in the header data and is transmitted from the ultrasound diagnostic apparatus 10 to the image processing apparatus 12. The image processing unit 54 generates the ultrasound images 62, 64, 66, and 68 by applying the first image processing to the above-described 4D data in accordance with the information indicating the first image processing included in the header data. The display controller 56 displays the ultrasound images 62, 64, 66, and 68 on the screen 70. It can be said that the ultrasound images 62, 64, 66, and 68 are each an example of an image corresponding to a fourth ultrasound image.

For example, the display controller 56 displays the ultrasound image 72 and the ultrasound image group 74 side by side on the screen 70. In the example shown in FIG. 10, the display controller 56 sets a display size of the ultrasound image group 74 to be smaller than a display size of the ultrasound image 72, and displays the ultrasound image 72 and the ultrasound image group 74 on the screen 70. This display example is merely an example, and the display controller 56 may set the display size of the ultrasound image 72 to be the same as the display size of the ultrasound image group 74, and display the ultrasound image 72 and the ultrasound image group 74 on the screen 70. Of course, the display controller 56 may set the display size of the ultrasound image group 74 to be larger than the display size of the ultrasound image 72, and display the ultrasound image 72 and the ultrasound image group 74 on the screen 70. In addition, the user (for example, a doctor) of the image processing apparatus 12 may designate the display size of each of the ultrasound image 72 and the ultrasound image group 74, and the display controller 56 may display the ultrasound image 72 and the ultrasound image group 74 on the screen 70 in the display size designated by the user.

Since the high-speed communication path is used as the communication path N, the ultrasound image 72 is displayed on the screen 70 in real time. For example, the ultrasound image 72 is displayed on the display of the image processing apparatus 12 at the same timing as or substantially the same timing as a timing at which the ultrasound images 62, 64, 66, and 68 are displayed on the display of the ultrasound diagnostic apparatus 10. As a result, the user (for example, a doctor) of the image processing apparatus 12 can observe the second ultrasound image generated based on the Raw data in real time even in a case in which the user is not present near the ultrasound diagnostic apparatus 10. In addition, the user of the image processing apparatus 12 can observe the first ultrasound image in real time even in a case in which the user is not present near the ultrasound diagnostic apparatus 10. For example, the user of the image processing apparatus 12 can perform diagnosis or the like by observing the first ultrasound image and the second ultrasound image in real time at a location (for example, a remote location) away from the ultrasound diagnostic apparatus 10.

In addition, as shown in FIG. 10, by displaying the first ultrasound image and the second ultrasound image side by side, the user of the image processing apparatus 12 can compare the first ultrasound image and the second ultrasound image in real time. For example, the CV-3D image displayed on the display of the ultrasound diagnostic apparatus 10 and the CV-4D image different from the CV-3D image are displayed side by side on the screen 70. As a result, the user can compare the CV-3D image and the CV-4D image displayed on the display of the ultrasound diagnostic apparatus 10 in real time.

The ultrasound image 72 is merely an example of the second ultrasound image, and a second ultrasound image other than the ultrasound image 72 may be generated and displayed. For example, the image processing unit 54 may generate a three-dimensional ultrasound image showing a stationary tissue in a three-dimensional manner, a two-dimensional ultrasound image (that is, a cross-sectional image) showing a stationary tissue in a planar manner, or a two-dimensional ultrasound image showing a state in which the tissue is moving, as the second ultrasound image. The display controller 56 displays the second ultrasound image generated by the image processing unit 54 on the screen 70. For example, in a case in which the user of the image processing apparatus 12 designates the second image processing, the image processing unit 54 generates the second ultrasound image by applying the second image processing designated by the user to the Raw data.

For example, in a case in which the user of the image processing apparatus 12 designates a desired cross section or angle by using the input unit 50, the image processing unit 54 generates a second ultrasound image representing the designated cross section or generates a second ultrasound image in a case in which the tissue is viewed from the designated angle. These second ultrasound images are displayed on the display of the output unit 48. As a result, the user can observe a second ultrasound image representing the cross section that the user desires to see or observe a tissue from the angle that the user desires to see.

In a case in which the user designates a cross section suitable for the measurement, a second ultrasound image representing the cross section is generated, and the measurement is performed on the second ultrasound image. As a result, the user can measure the cross section that the user desires to measure in real time at a remote location.

The display controller 56 may display the second ultrasound image on the display of the output unit 48 in accordance with the designated display mode. The display controller 56 may display mode identification information for identifying the display mode on the display of the output unit 48. For example, the display mode is a LIVE mode, a CINE mode, or a LIVE OFF mode.

The LIVE mode is a mode in which the second ultrasound image generated by applying the second image processing to the Raw data while receiving the Raw data from the ultrasound diagnostic apparatus 10 is displayed. The LIVE mode corresponds to an example of a first mode. For example, the LIVE mode is a mode in which the second image processing is applied in real time to the Raw data acquired by the ultrasound diagnostic apparatus 10, and the second ultrasound image generated by the application of the second image processing is displayed in real time. In a case in which the Raw data is transmitted in real time from the ultrasound diagnostic apparatus 10 to the image processing apparatus 12 via the communication path N, the image processing unit 54 generates the second ultrasound image by applying the second image processing to the Raw data. The display controller 56 displays the second ultrasound image on the display of the output unit 48. As a result, the second ultrasound image is displayed in real time. For example, the second ultrasound image as a video image is displayed in real time.

The CINE mode is a mode in which the second ultrasound image generated by receiving the Raw data to be stored in the main memory 42 and applying the second image processing to the Raw data is displayed. The CINE mode corresponds to an example of a second mode. For example, in a case in which the user of the image processing apparatus 12 designates the Raw data stored in the main memory 42 and issues an instruction to apply the second image processing, the image processing unit 54 generates the second ultrasound image by reading the Raw data designated by the user from the main memory 42 and applying the second image processing to the Raw data. The display controller 56 displays the second ultrasound image on the display of the output unit 48. The second ultrasound image displayed in accordance with the CINE mode is not necessarily an image displayed in real time. For example, a mode in which the recorded second ultrasound image is displayed is the CINE mode.

The LIVE OFF mode is a mode in which the second ultrasound image is displayed in a still state. The LIVE OFF mode corresponds to an example of a third mode. For example, in a case in which the user designates the LIVE OFF mode in a case in which the display mode is the LIVE mode, the display controller 56 displays the second ultrasound image that was displayed during the LIVE mode on the display of the output unit 48 in a still state.

For example, in a case in which the user of the image processing apparatus 12 designates the display mode, the display controller 56 displays the second ultrasound image on the display of the output unit 48 in accordance with the display mode designated by the user.

The display mode may be designated in advance. For example, the display mode may be designated in advance for each diagnosis site, may be designated in advance for each analysis type, or may be designated in advance for each image type. The display controller 56 displays the second ultrasound image on the display of the output unit 48 in accordance with the display mode designated in advance. Even in this case, in a case in which the user designates the display mode, the display controller 56 may display the second ultrasound image on the display of the output unit 48 in accordance with the display mode designated by the user.

The mode identification information is, for example, an image or a character string representing the display mode. An indicator 76 shown in FIG. 10 is an example of the mode identification information.

The indicator 76 includes an image and a character string. The display controller 56 displays the indicator 76 on the screen 70 by changing at least one of a color, a shape, or a size of the image included in the indicator 76 according to the display mode. For example, a color of an image representing the LIVE mode is red, a color of an image representing the CINE mode is blue, and a color of an image representing the LIVE OFF mode is green.

In the example shown in FIG. 10, the ultrasound image 72 is displayed in accordance with the LIVE mode. Therefore, the color of the image included in the indicator 76 is red. In addition, the character string "LIVE" is displayed on the screen 70.

The user of the image processing apparatus 12 may designate a display mode of the first ultrasound image. In this case, the display controller 56 displays the first ultrasound image on the display of the output unit 48 in accordance with the display mode designated by the user. For example, in the example shown in FIG. 10, in a case in which the LIVE mode is designated as the display mode of the first ultrasound image, the display controller 56 displays the ultrasound image group 74 on the screen 70 in accordance with the LIVE mode.

Figure 11:
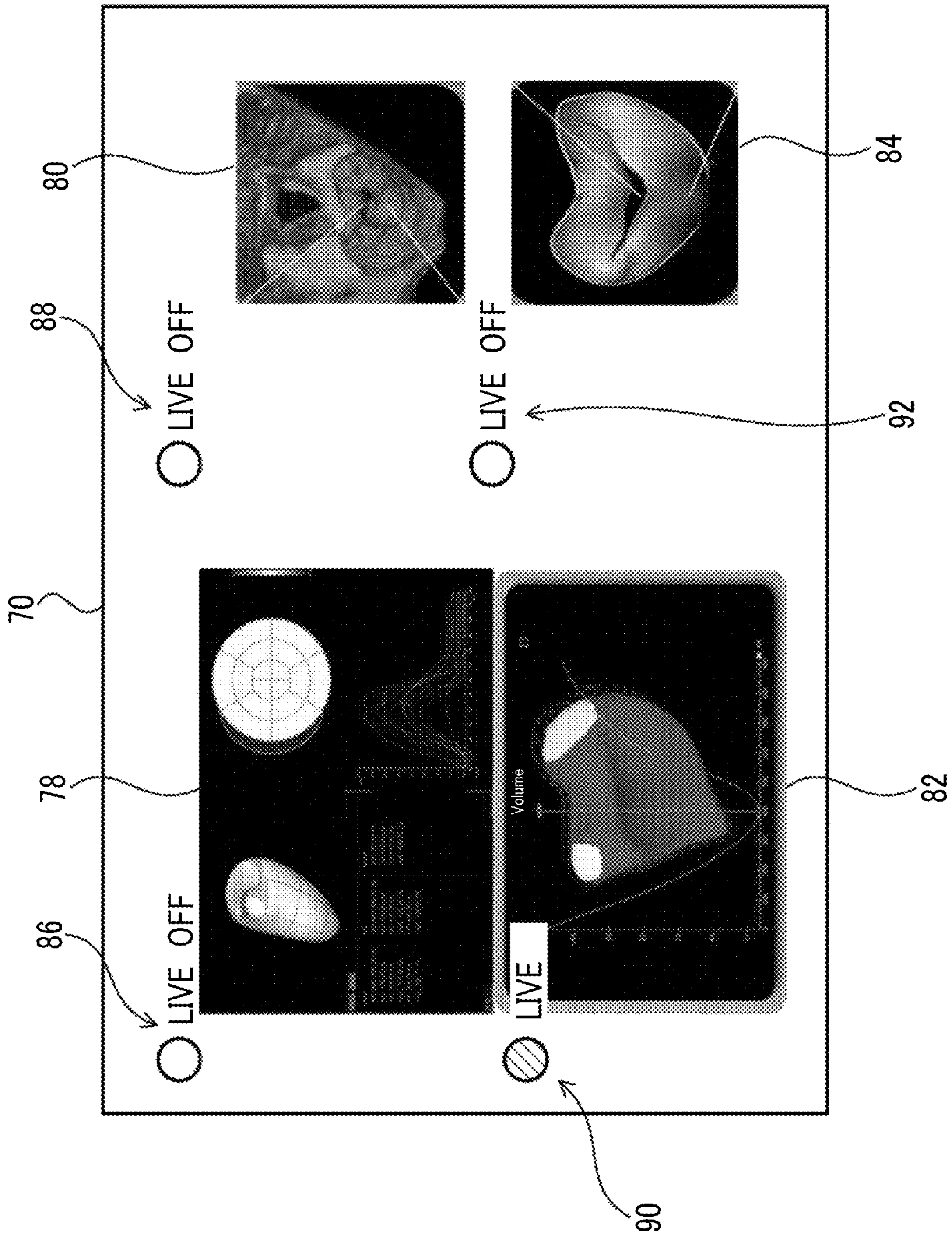
FIG. 11 is a diagram showing a display example of a second ultrasound image.

Another second ultrasound image is shown in FIG. 11. Ultrasound images 78, 80, 82, and 84 are the second ultrasound images and are displayed on the screen 70. The image processing unit 54 generates the ultrasound images 78, 80, 82, and 84 by applying the second image processing to the above-described 4D data. The ultrasound images 78, 80, 82, and 84 are ultrasound images different from the ultrasound images 62, 64, 66, and 68 displayed on the display of the ultrasound diagnostic apparatus 10.

The ultrasound images 78, 80, 82, and 84 are each an example of the CV-4D image. For example, the ultrasound image 78 includes a 16-segment bullseye chart of the left ventricle and an image representing the myocardium. The ultrasound image 80 is an image representing the aortic valve and the mitral valve (for example, an image generated by volume rendering). The ultrasound image 82 includes an image showing a surface of the right ventricular endocardial model (for example, an image generated by surface rendering) and a volume curve. The ultrasound image 84 is an image showing a surface of the mitral valve model (for example, an image generated by surface rendering).

The ultrasound images 78, 80, and 84 are displayed in accordance with the LIVE OFF mode. The ultrasound image 82 is displayed in accordance with the LIVE mode.

An indicator 86 is mode identification information of the display mode of the ultrasound image 78, and is displayed around the ultrasound image 78. An indicator 88 is mode identification information of the display mode of the ultrasound image 80, and is displayed around the ultrasound image 80. An indicator 90 is mode identification information of the display mode of the ultrasound image 82, and is displayed around the ultrasound image 82. An indicator 92 is mode identification information of the display mode of the ultrasound image 84, and is displayed around the ultrasound image 84.

For example, in a case in which the user of the image processing apparatus 12 designates the display mode for each second ultrasound image, the display controller 56 displays each second ultrasound image on the screen 70 in accordance with the display mode of each second ultrasound image. Of course, the display controller 56 may display all the second ultrasound images on the screen 70 in accordance with the same display mode.

The ultrasound images 78, 80, and 84 are images generated based on the same 4D data. In the present embodiment, in a case in which a plurality of the ultrasound images are generated based on the same 4D data, each ultrasound image can be displayed by making the modes of the individual ultrasound images the same or different from each other. Here, as an example, the ultrasound image 82 is displayed in accordance with the LIVE mode, but, in response to the user's instruction, the ultrasound image (for example, the ultrasound image 78) other than the ultrasound image 82 may be displayed in accordance with the LIVE mode, and the ultrasound image 82 may be displayed in accordance with the LIVE OFF mode. In this way, the modes of the respective ultrasound images generated based on the same 4D data can be individually switched. In addition, the indicator enables the user to determine not only whether or not the display mode is the LIVE mode but also whether or not the display mode is the CINE mode.

Figure 12:
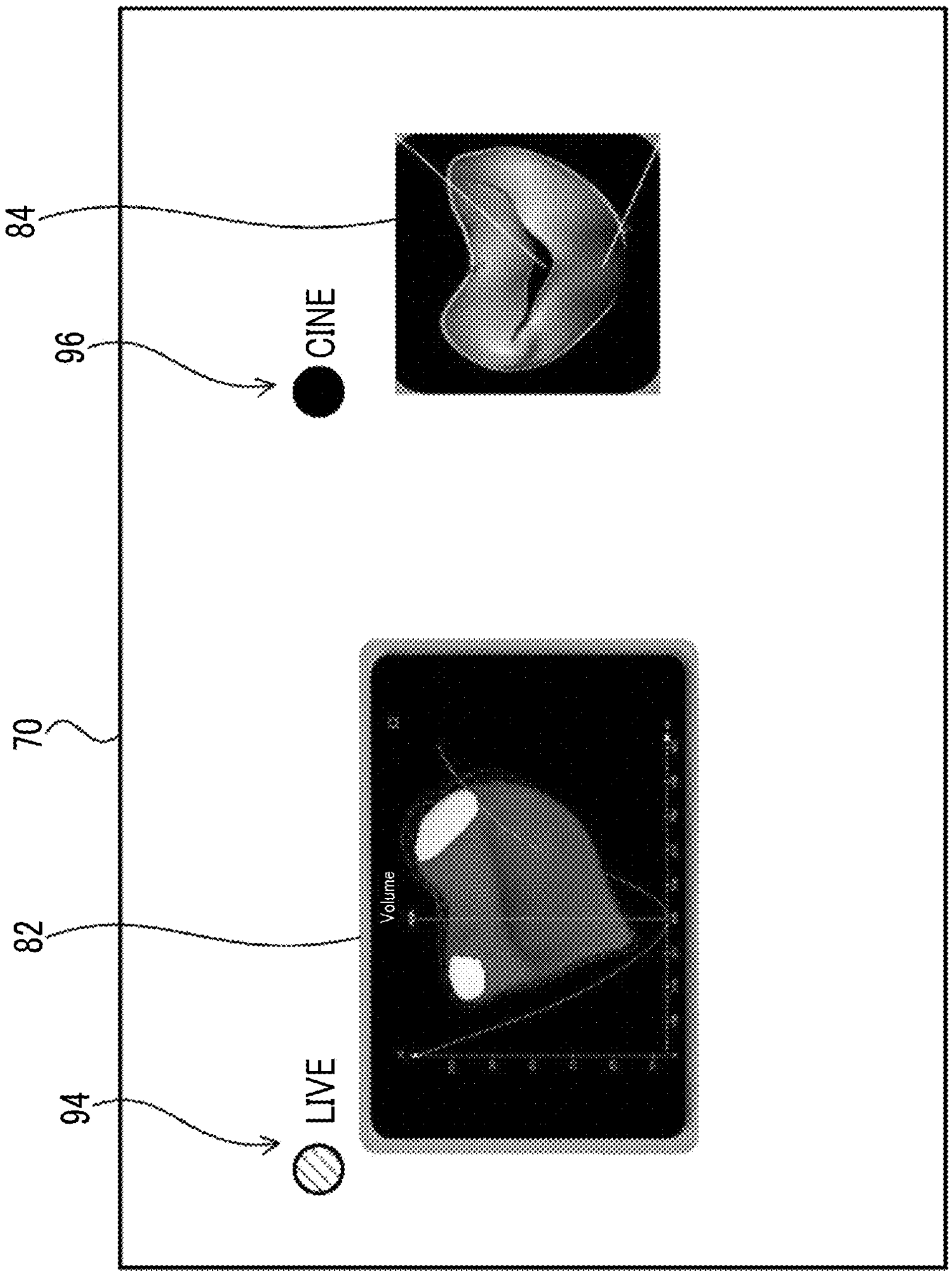
FIG. 12 is a diagram showing a display example of a second ultrasound image.

Another display example of the second ultrasound image is shown in FIG. 12. The ultrasound images 82 and 84 are the second ultrasound images and are displayed on the screen 70. The ultrasound images 82 and 84 shown in FIG. 12 are the same as the ultrasound images 82 and 84 shown in FIG. 11.

An indicator 94 is mode identification information of the display mode of the ultrasound image 82, and is displayed around the ultrasound image 82. An indicator 96 is mode identification information of the display mode of the ultrasound image 84, and is displayed around the ultrasound image 84.

In the example shown in FIG. 12, the ultrasound image 82 is displayed in accordance with the LIVE mode. The ultrasound image 84 is displayed in accordance with the CINE mode.

For example, by changing the display mode according to the purpose of the diagnosis or the examination, the user of the image processing apparatus 12 can observe the second ultrasound image displayed in accordance with the display mode according to the purpose and perform the diagnosis or the examination.

Figure 13:
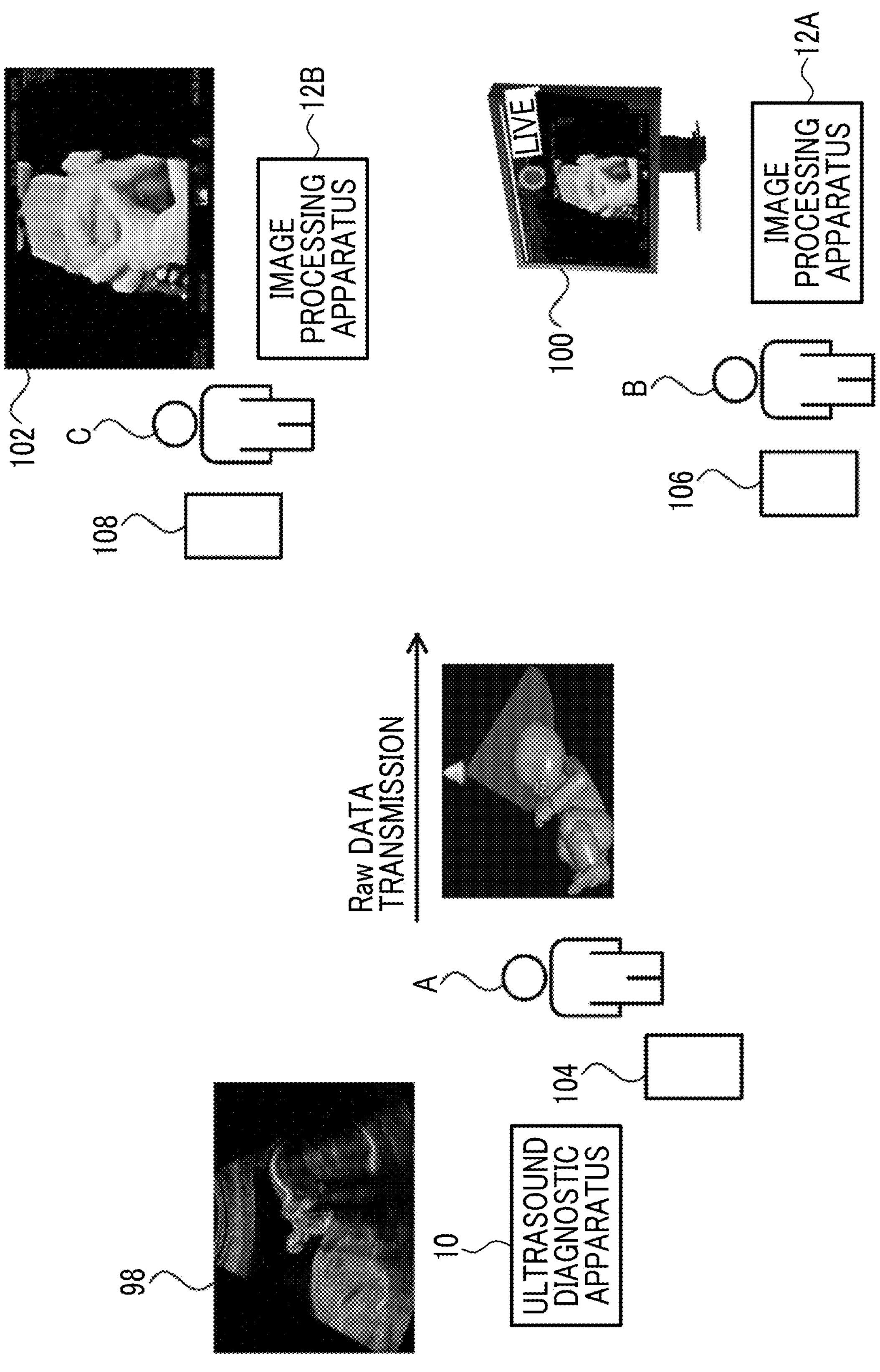
FIG. 13 is a diagram for describing an application example of the embodiment.

Hereinafter, an application example of the present embodiment will be described with reference to FIG. 13. FIG. 13 is a diagram for describing the application example.

For example, the ultrasound diagnostic apparatus 10 is used for obstetric examination. The first image processing and the second image processing are image processing related to the obstetric examination. That is, the first image processing and the second image processing are image processing suitable for the obstetric examination and gynecology or image processing of generating an ultrasound image used for the obstetric examination.

For example, in the obstetrics department, not only the doctor but also a third party such as a family member of the subject (patient) has a request to see the ultrasound image. For example, in a case in which a third party can go to a location where the subject is being imaged by the ultrasound diagnostic apparatus 10, the third party can see the first ultrasound image displayed on the display of the ultrasound diagnostic apparatus 10 to satisfy the third party's request.

However, the third party may not always be able to go to the location where the subject is being imaged by the ultrasound diagnostic apparatus 10, and may want to see the ultrasound image of the subject at a remote location. In such a case, in a case in which the processing according to the present embodiment is executed, the third party can view the second ultrasound image at a remote location without going to the location.

In addition, the ultrasound image that the third party wants to see and the ultrasound image necessary for the examination using the ultrasound diagnostic apparatus 10 are not necessarily the same. In this case, by executing the processing according to the present embodiment, the second ultrasound image desired by the third party is generated and displayed, thereby satisfying the third party's request.

In the example shown in FIG. 13, an examination technician A operates the ultrasound diagnostic apparatus 10 in the obstetrics department to acquire Raw data (for example, 4D data). The ultrasound diagnostic apparatus 10 generates a first ultrasound image 98 by applying first image processing to the Raw data. The first ultrasound image 98 is an ultrasound image required for the obstetric examination. The examination technician A performs the examination or the like based on the first ultrasound image 98. The Raw data is transmitted from the ultrasound diagnostic apparatus 10 to the image processing apparatus 12 via the communication path N.

Image processing apparatuses 12A and 12B are shown in FIG. 13. The image processing apparatuses 12A and 12B have the same configurations as the image processing apparatus 12. The image processing apparatuses 12A and 12B are apparatuses installed at separate locations. For example, the image processing apparatus 12A is used to display the ultrasound image to a doctor B. The image processing apparatus 12B is used to display the ultrasound image to a family C. The family C is a family of the subject from which the Raw data is acquired.

For example, a second ultrasound image 100 for the doctor B to perform the diagnosis, the examination, or the like is generated and displayed by the image processing unit 54 of the image processing apparatus 12A. That is, the second image processing for generating the second ultrasound image 100 is executed by the image processing unit 54 of the image processing apparatus 12A. The doctor B can refer to the second ultrasound image 100 at the remote location to perform the diagnosis, the examination, or the like.

For example, a second ultrasound image 102 that the family C wants to see is generated and displayed by the image processing unit 54 of the image processing apparatus 12B. That is, the second image processing for generating the second ultrasound image 102 is executed by the image processing unit 54 of the image processing apparatus 12B. For example, the family C can refer to the second ultrasound image 102 at the remote location to check the growth of the fetus or the like.

In addition, terminal devices 104, 106, and 108 may be used. The terminal devices 104, 106, and 108 are a PC, a tablet PC, a smartphone, or a mobile phone, and are devices capable of transmitting and receiving voice.

For example, the examination technician A uses the terminal device 104, and the doctor B uses the terminal device 106, and the examination technician A and the doctor B communicate in real time. In this manner, the examination technician A and the doctor B can communicate with each other by voice while referring to the ultrasound image. For example, the doctor B can instruct the examination technician A to image a site necessary for the diagnosis by voice.

Similarly, the family C uses the terminal device 108 to communicate the examination technician A in real time. For example, the family C can tell the image that the family C wants to see to the examination technician A by voice.

Although the obstetrics department is described as an example, the same effects can be obtained even in a medical department other than the obstetrics department to which the present embodiment is applied.

The image processing to be executed by the ultrasound diagnostic apparatus 10 may be instructed to the ultrasound diagnostic apparatus 10 from the image processing apparatus 12. For example, the image processing apparatus 12 includes a user interface that receives selection of the third image processing. The third image processing is image processing to be executed by the ultrasound diagnostic apparatus 10.

The user interface is realized by the output unit 48 and the input unit 50. The display controller 56 displays on display of a screen for selecting the third image processing on the display of the output unit 48. For example, a list of a plurality of different third image processing is displayed on the screen. The user can select the third image processing on the screen by operating the input unit 50. Of course, the third image processing may be selected by voice. A cross section or a diagnosis site to be displayed may be designated by the user interface.

The communication unit 38 transmits the control information indicating the selection received by the user interface to the ultrasound diagnostic apparatus 10 via the communication path N. That is, in a case in which the third image processing is selected by the user on the screen, the communication unit 38 transmits the control information indicating the third image processing selected by the user to the ultrasound diagnostic apparatus 10 via the communication path N. Similarly, in a case in which the third image processing is selected by voice, the communication unit 38 transmits the control information indicating the selected third image processing to the ultrasound diagnostic apparatus 10.

The communication unit 34 of the ultrasound diagnostic apparatus 10 receives the control information via the communication path N. The image processing unit 20 of the ultrasound diagnostic apparatus 10 generates a third ultrasound image by applying the third image processing indicated by the control information to the Raw data. The display controller 30 of the ultrasound diagnostic apparatus 10 displays the third ultrasound image on the display unit 24.

The Raw data to which the third image processing is applied may be selected by, for example, the user of the image processing apparatus 12 or the user of the ultrasound diagnostic apparatus 10. For example, the image processing unit 20 generates the third ultrasound image by applying the third image processing to the Raw data stored in the storage unit 36 of the ultrasound diagnostic apparatus 10.

For example, on the day of the examination, the CV-3D image is displayed as the first ultrasound image on the display of the ultrasound diagnostic apparatus 10, but on a later date, an image other than the CV-3D image is generated and displayed as the third ultrasound image. In this manner, more detailed analysis or examination than on the day of the examination can be performed by using the ultrasound diagnostic apparatus 10.

According to the embodiment described above, it is possible to realize the real-time diagnosis at a remote location. For example, the doctor or the like can observe or analyze the ultrasound image in real time at a remote location. In addition, the doctor or the like can observe an image that the doctor or the like wants to see in real time by giving an instruction of the image that the doctor or the like wants to see (for example, a desired site or angle) to the user (for example, the examination technician) of the ultrasound diagnostic apparatus 10 in real time. As a result, it is possible to reduce a frequency of re-examination using the ultrasound diagnostic apparatus 10. As a result, it is possible to reduce a burden on the doctor, the examination technician, and the subject.

In addition, in a case in which the image processing apparatus 12 has an image processing function higher than that of the ultrasound diagnostic apparatus 10, the image processing apparatus 12 can realize image processing that cannot be realized by the ultrasound diagnostic apparatus 10 in real time. For example, even in a case in which the ultrasound diagnostic apparatus 10 does not have a function of realizing 4D image processing for a circulatory system, in a case in which the image processing apparatus 12 has the function, the image processing apparatus 12 can execute the 4D image processing for a circulatory system in real time. The same can be said for 4D image processing for obstetrics. For example, even in a case in which the ultrasound diagnostic apparatus 10 is a portable ultrasound diagnostic apparatus and does not have a high-performance function, the high-performance function can be realized by the image processing apparatus 12. In addition, an image or the like in which an angle is changed can be checked at a remote location.

In addition, the ultrasound diagnostic system according to the present embodiment may be used for education or training of the examination technician, the doctor, or the like. For example, a skilled technician operates the ultrasound diagnostic apparatus 10 to acquire the Raw data, and the second ultrasound image based on the Raw data is displayed on the display of the image processing apparatus 12. A person who receives the education can receive explanation or the like from the skilled technician while observing the second ultrasound image displayed on the display of the image processing apparatus 12 in real time.

In the present embodiment, the data of the first ultrasound image itself may be transmitted from the ultrasound diagnostic apparatus 10 to the image processing apparatus 12 via the communication path, and the first ultrasound image may be displayed on the display of the image processing apparatus 12.

The signal processing unit 18, the image processing unit 20, the display processing unit 22, the controller 28, the display controller 30, and the conversion unit 32 can be realized by using hardware resources such as a processor and an electronic circuit. A device such as a memory may be used as necessary for realizing the above-described configuration. The signal processing unit 18, the image processing unit 20, the display processing unit 22, the controller 28, the display controller 30, and the conversion unit 32 may be realized by, for example, a computer. That is, all or a part of the signal processing unit 18, the image processing unit 20, the display processing unit 22, the controller 28, the display controller 30, and the conversion unit 32 may be realized by cooperation between hardware resources, such as a central processing unit (CPU) or a memory included in a computer, and software (program) that defines the operation of the CPU or the like. The program is stored in the storage unit 36 of the ultrasound diagnostic apparatus 10 or other storage device through a recording medium, such as a CD or a DVD, or a communication path, such as a network. As another example, the signal processing unit 18, the image processing unit 20, the display processing unit 22, the controller 28, the display controller 30, and the conversion unit 32 may be realized by a digital signal processor (DSP), an application specific integrated circuit (ASIC), a field programmable gate array (FPGA), or the like. A graphics processing unit (GPU)

or the like may be used. The signal processing unit 18, the image processing unit 20, the display processing unit 22, the controller 28, the display controller 30, and the conversion unit 32 may be realized by a single device. Each function of the signal processing unit 18, the image processing unit 20, the display processing unit 22, the controller 28, the display controller 30, and the conversion unit 32 may be realized by one or a plurality of devices.

The reception unit 40, the memory controller 44, the image processing unit 54, and the display controller 56 can be realized by using hardware resources such as a processor and an electronic circuit. A device such as a memory may be used as necessary for realizing the above-described configuration. The reception unit 40, the memory controller 44, the image processing unit 54, and the display controller 56 may be realized by, for example, a computer. That is, all or a part of the reception unit 40, the memory controller 44, the image processing unit 54, and the display controller 56 may be realized by cooperation between hardware resources, such as a central processing unit (CPU) or a memory included in a computer, and software (program) that defines the operation of the CPU or the like. The program is stored in the main memory 42 of the image processing apparatus 12 or another storage device through a recording medium, such as a CD or a DVD, or a communication path, such as a network. As another example, the reception unit 40, the memory controller 44, the image processing unit 54, and the display controller 56 may be realized by a digital signal processor (DSP), an application specific integrated circuit (ASIC), a field programmable gate array (FPGA), or the like. A graphics processing unit (GPU) or the like may be used. The reception unit 40, the memory controller 44, the image processing unit 54, and the display controller 56 may be realized by a single device. Each function of the reception unit 40, the memory controller 44, the image processing unit 54, and the display controller 56 may be realized by one or a plurality of devices.

What is claimed is:

1. An ultrasound diagnostic system comprising:

an ultrasound diagnostic apparatus; and an image processing apparatus, wherein the ultrasound diagnostic apparatus includes an acquisition unit that acquires raw data by transmitting and receiving ultrasonic waves, a first image processing unit that generates a first ultrasound image by applying first image processing to the raw data, a first display controller that displays the first ultrasound image generated by the first image processing unit on a first display of the ultrasound diagnostic apparatus, and a first transmission unit that transmits the raw data, to which the first image processing has not been applied by the first image processing unit, to the image processing apparatus via a communication path, and wherein the image processing apparatus includes a second reception unit that receives the raw data transmitted by the first transmission unit via the communication path, a second image processing unit that generates a second ultrasound image different from the first ultrasound image displayed on the first display of the ultrasound diagnostic apparatus by applying second image processing different from the first image processing to the raw data received by the second reception unit, a second display controller that displays the second ultrasound image generated by the second image processing unit on a second display of the image processing apparatus, a user interface that receives selection of the second image processing, and a second transmission unit that transmits to the ultrasound diagnostic apparatus, via the communication path, control information for causing the ultrasound diagnostic apparatus to apply the second image processing, identical to the second imaging processing applied to the raw data in the image processing apparatus, and wherein the ultrasound diagnostic apparatus further includes a first reception unit that receives the control information transmitted by the second transmission unit via the communication path, the first image processing unit generates a third ultrasound image by applying the second image processing indicated by the control information received by the first reception unit to the raw data, and the first display controller displays the third ultrasound image on the first display.

2. The ultrasound diagnostic system according to claim 1, wherein the second image processing unit generates a three-dimensional ultrasound image as the second ultrasound image based on the raw data.

3. The ultrasound diagnostic system according to claim 1, wherein the second image processing unit generates the second ultrasound image by applying the second image processing to the raw data in response to the selection received by the user interface.

4. The ultrasound diagnostic system according to claim 1, wherein the first transmission unit transmits information indicating the first image processing to the image processing apparatus via the communication path, the second reception unit receives the information indicating the first image processing transmitted by the first transmission unit via the communication path, the second image processing unit generates the second ultrasound image by applying the second image processing to the raw data and generates the first ultrasound image by applying the first image processing to the raw data in accordance with the information indicating the first image processing, and the second display controller displays the second ultrasound image and the first ultrasound image side by side on the second display.

5. The ultrasound diagnostic system according to claim 1, wherein the first transmission unit transmits header data including information indicating the first image processing to the image processing apparatus via the communication path in association with the raw data, the second reception unit receives the raw data and the header data transmitted by the first transmission unit via the communication path, the second image processing unit generates a fourth ultrasound image by applying the first image processing to the raw data in accordance with the information indicating the first image processing included in the header data, and the second display controller displays the fourth ultrasound image on the second display.

6. The ultrasound diagnostic system according to claim 1, wherein the second display controller displays the second ultrasound image on the second display in accordance with a designated display mode, and displays mode identification information for identifying the display mode on the second display.

7. The ultrasound diagnostic system according to claim 6, wherein the display mode is any one of a first mode in which the second ultrasound image generated by applying the second image processing to the raw data while receiving the raw data is displayed, a second mode in which the second ultrasound image generated by receiving the raw data to be stored in a memory and applying the second image processing to the raw data is displayed, or a third mode in which the second ultrasound image is displayed in a still state.

8. The ultrasound diagnostic system according to claim 1, wherein the ultrasound diagnostic apparatus is used for circulatory organ examination, and the first image processing and the second image processing are image processing related to the circulatory organ examination.

9. The ultrasound diagnostic system according to claim 1, wherein the ultrasound diagnostic apparatus is used for obstetric examination, and the first image processing and the second image processing are image processing related to the obstetric examination.

10. An image processing apparatus comprising:

a second reception unit that receives raw data, via a communication path, from an ultrasound diagnostic apparatus that acquires the raw data through transmission and reception of ultrasonic waves and generates a first ultrasound image by applying first image processing to the raw data;

a second image processing unit that generates a second ultrasound image different from the first ultrasound image by applying second image processing different from the first image processing to the raw data received by the second reception unit;

a second display controller that displays the second ultrasound image generated by the second image processing unit on a display;

a user interface that receives selection of the second image processing; and a second transmission unit that transmits to the ultrasound diagnostic apparatus, via the communication path, control information for causing the ultrasound diagnostic apparatus to apply the second image processing, identical to the second imaging processing applied to the raw data in the image processing apparatus, wherein the ultrasound diagnostic apparatus generates a third ultrasound image by applying the second image processing indicated by the control information to the raw data.

* * * * *